US009034632B2

(12) United States Patent
Mancinelli et al.

(10) Patent No.: US 9,034,632 B2
(45) Date of Patent: May 19, 2015

(54) COMPOSITIONS AND METHODS FOR CULTURING MICROORGANISMS

(71) Applicant: HelioBiosys, Inc., Woodside, CA (US)

(72) Inventors: Rocco Mancinelli, Woodside, CA (US); David Smernoff, Portola Valley, CA (US)

(73) Assignee: HelioBioSys, Inc., Woodside, CA (US)

( * ) Notice: Subject to any disclaimer, the term of this patent is extended or adjusted under 35 U.S.C. 154(b) by 0 days.

(21) Appl. No.: 13/719,647

(22) Filed: Dec. 19, 2012

(65) Prior Publication Data

US 2013/0183732 A1 Jul. 18, 2013

Related U.S. Application Data

(63) Continuation of application No. PCT/US2011/042712, filed on Jun. 30, 2011.

(60) Provisional application No. 61/497,913, filed on Jun. 16, 2011, provisional application No. 61/360,838, filed on Jul. 1, 2010.

(51) Int. Cl.
| *C12N 1/12* | (2006.01) |
| *C12N 1/38* | (2006.01) |
| *C12N 1/14* | (2006.01) |
| *C12N 1/20* | (2006.01) |
| *C12N 9/04* | (2006.01) |
| *C12N 9/88* | (2006.01) |
| *C12P 7/06* | (2006.01) |
| *C12P 7/14* | (2006.01) |
| *C12P 7/16* | (2006.01) |
| *C12P 39/00* | (2006.01) |
| *C12N 1/16* | (2006.01) |

(52) U.S. Cl.
CPC .. *C12N 1/38* (2013.01); *C12N 1/14* (2013.01); *C12N 1/20* (2013.01); *C12N 9/0006* (2013.01); *C12N 9/88* (2013.01); *C12P 7/06* (2013.01); *C12P 7/065* (2013.01); *C12P 7/14* (2013.01); *C12P 7/16* (2013.01); *C12P 39/00* (2013.01); *C12N 1/12* (2013.01); *C12N 1/16* (2013.01); *Y02E 50/10* (2013.01); *Y02E 50/17* (2013.01); *Y10S 435/946* (2013.01)

(58) Field of Classification Search
None
See application file for complete search history.

(56) References Cited

U.S. PATENT DOCUMENTS

| 4,764,471 | A | 8/1988 | Ripka |
| 6,596,521 | B1 | 7/2003 | Chang |
| 7,022,354 | B1 | 4/2006 | Sato et al. |
| 7,662,617 | B2 | 2/2010 | Rush |
| 7,807,427 | B2 * | 10/2010 | Koshland, Jr. ............... 435/166 |
| 8,518,690 | B2 * | 8/2013 | Beliaev et al. ............... 435/262 |
| 2008/0124286 | A1 * | 5/2008 | Lisson ........................ 424/61 |

FOREIGN PATENT DOCUMENTS

| WO | WO-01/02534 A1 | 1/2001 |
| WO | WO-2012/003402 A2 | 1/2012 |

OTHER PUBLICATIONS

ATCC Catalogue. ATCC Bacteria and Bacteriophages. 19th edition, 1996, pp. 123, 407, 500, 511 and 516.*
Fei, Xu Fu. "Principle factors affecting the growth and N2 fixation of cyanobacterium *Trichodesmium* sp". PhD Thesis, abstract, publication date 2004, pp. 1-2 retrieved at http://espace.library.uq.edu.au/view/UQ:106967.*
Ladas et al. Photosynthetica 200, 38 (3): 343-348.*
Agawin et al. Limnology and Oceanography, 2007, 52(5): 2233-2248.*
McKay et al. Proceeding from the 2010 AGU Ocean Science Meeting, Feb. 2010, abstract; STN file PQSITECH accession No. 2010:562010.*
Guillard, Robert R. L., et al., "Studies of marine planktonic diatoms. I. Cyclotella nana Hustedt and Detonula confervacea Cleve.", *Canadian Journal of Microbiology, 8*, (1962), 229-239.
Leao, Pedro N., et al., "Allelopathy in freshwater cyanobacteria", *Crit. Rev. Microbiol.*, 35(4), (2009), 271-282.
Lin, Yan, et al., "Ethanol Fermentation from Biomass Resources: Current State and Prospects", *Appl. Microbiol. Biotechnol.*, 69, (2006), 627-642.
Nasser, Abdel A., et al., "Comparative Study of Salt Tolerance in *Saccharomyces cerevisiae* and *Pichia pastoris* Yeast Strains", *Advances in Bioresearch*, 1(1), (2010), 169-176.
Ohta, K., et al., "Metabolic engineering of *Klebsiella oxytoca* M5A1 for ethanol production from xylose and glucose", *Appl. Environ. Microbiol,*, 57(10), (1991), 2810-2815.
"International Application Serial No. PCT/US2011/042712, International Preliminary Report on Patentability dated Jan. 8, 2013", 8 pgs.
"International Application Serial No. PCT/US2011/042712, International Search Report mailed Mar. 28, 2012", 4 pgs.
"International Application Serial No. PCT/US2011/042712, Written Opinion mailed Mar. 28, 2012", 7 pgs.

(Continued)

*Primary Examiner* — Vera Afremova

(74) *Attorney, Agent, or Firm* — Schwegman Lundberg & Woessner, P.A.

(57) ABSTRACT

This disclosure provides compositions and methods for culturing microorganisms. The disclosure includes mixtures of different microorganisms, especially mixtures of cyanobacteria with fermentative microorganisms. For example, methods and compositions related to co-cultures of yeast and cyanobacteria are provided. Also provided are feedstocks derived from cyanobacteria as well as methods of making such feedstocks and methods of culturing microorganisms in such feedstocks.

8 Claims, 7 Drawing Sheets

(56) References Cited

OTHER PUBLICATIONS

Dellomonaco, Clementina, et al., "The path to next generation biofuels: successes and challenges in the era of synthetic biology", *Microbial Cell Factories*, 9:3, (2010), 1-15.

Fett, W. F., et al., "Chapter 6—Biopolymers from Fermentation", *In: Agricultural Materials as Renewable Resources: Nonfood and Industrial Applications* (ACS Symposium Series 647), Fuller, G., et al., Editors, American Chemical Society, (1996), 76-87.

Guillard, R. R. L., et al., "*Stichochrysis immobilis* is a diatom, not a chrysophyte", Phycologia, 32(3), (1993), 234-236.

Guillard, Robert R. L., "Culture of phytoplankton for feeding marine invertebrates", *In: Culture of Marine Invertebrate Animals,* Smith W. L. and Chanley M. H., (Editors), Plenum Press, (1975), 29-60.

Guillard, Robert R. L., et al., "Studies of marine planktonic diatoms, I. Cyclotella nana Hustedt and Detonula confervacea Cleve.", *Canadian Journal of Microbiology*, 8, (1962), 229-239.

\* cited by examiner

COMPOSITIONS AND METHODS FOR CULTURING MICROORGANISMS

CROSS-REFERENCE

This application is a continuation of PCT Application No. US2011/42712, filed on Jun. 30, 2011, which claims the benefit of, and priority to, U.S. Provisional Application No. 61/360,838, filed on Jul. 1, 2010, and U.S. Provisional Application No. 61/497,913, filed on Jun. 16, 2011, the full disclosures of each of which are incorporated herein in their entirety for all purposes.

BACKGROUND OF THE INVENTION

Biofuels and biopolymers have been increasingly developed for use in the energy and manufacturing sectors, respectively. Biofuels offer an attractive alternative to replace fossil fuels, which are expensive, in short supply, and capable of causing egregious environmental devastation, as underscored by the recent oil spill in the Gulf of Mexico as well as by trends in global warming. Biofuels are generally produced from plant materials, vegetable oils, animal fats, or recycled greases. Currently, starch (e.g., corn, wheat, barley, etc.) and sugar crops (e.g., sugarcane, beet, etc.) are the major feedstocks used for bioconversion to ethanol, a major biofuel. However, such field crops have drawbacks in that they have high costs and are non-sustainable.

Biopolymers offer an attractive replacement to conventional plastics, such as plastics derived from polystyrene or polyethylene, which are not biodegradable and which require significant resources to produce.

Despite their appeal, the production of biofuels and biopolymers can be problematic. Large amounts of energy and money are often needed, for example to grow crops, make fertilizers and pesticides, and process plants. Microorganisms offer the potential to produce biofuels or biopolymers. However, like plant-based biofuels, microorganism-based biofuels can also be an inefficient process. High financial and energy costs of producing feedstock can be one barrier to large-scale production of biofuels or biopolymers from microorganisms. There is therefore a need in the art for new microorganism cultures, as well as new methods of culturing microorganisms, especially methods and cultures that require relatively small amounts of energetic inputs.

SUMMARY OF THE INVENTION

In one aspect, this disclosure provides a culture comprising at least one fermentative microorganism selected from the group consisting of Saccharomycetes, *Saccharomyces*, *Schizosaccharomyces* and fermentative bacteria, wherein the medium of said culture comprises a salt concentration greater than 1%.

In a second aspect, this disclosure provides a culture comprising fermentative microorganisms and medium derived from a culture of cyanobacteria, wherein the medium of said culture comprises a salt concentration greater than 1%.

In a third aspect, this disclosure provides a culture comprising fermentative microorganisms and medium derived from a culture of cyanobacteria, wherein said culture is substantially free of cyanobacteria.

In a fourth aspect, this disclosure provides a culture comprising cyanobacteria and at least one fermentative microorganism selected from the group consisting of: Saccharomycetes, *Schizosaccharomyces* and fermentative bacteria.

In a fifth aspect, this disclosure provides a culture comprising cyanobacteria and fermentative microorganisms, wherein said fermentative microorganisms receive growth media from products released by said cyanobacteria.

In some embodiments wherein the culture comprises cyanobacteria, said cyanobacteria are genetically modified to produce a fermentation product. In further embodiments, said cyanobacteria are genetically modified to produce ethanol, butanol, or any alcohol. In still further embodiments, said cyanobacteria comprise exogenous genes encoding pyruvate decarboxylase and alcohol dehydrogenase. In some embodiments, said cyanobacteria do not comprise exogenous genes encoding pyruvate decarboxylase and alcohol dehydrogenase. In some embodiments, said cyanobacteria are cultured for greater than mid log phase growth. In some embodiments, said cyanobacteria were previously cultured in a medium comprising sea water or filtered sea water. In some embodiments, said cyanobacteria were previously cultured in the presence of solar energy. In yet other embodiments, said cyanobacteria were previously cultured under a light/dark regime. In yet other embodiments, said cyanobacteria were previously cultured in the absence of solar energy. In some embodiments, said cyanobacteria were previously cultured for greater than 1, 5, 10, 15, 20, 25, 30, 40, 45, 50, 55, 60, 70, 75, 80, 90, 100, 150, or 200 days. In yet other embodiments, greater than 5%, 10%, 15%, 20%, 25%, 30%, 35%, 40%, 45%, 50%, 55%, 60%, 65%, 70%, 75%, 80%, 85%, 90%, or 95% of said cyanobacteria are live organisms. In yet other embodiments, greater than 5%, 10%, 15%, 20%, 25%, 30%, 35%, 40%, 45%, 50%, 55%, 60%, 65%, 70%, 75%, 80%, 85%, 90%, or 95% of said cyanobacteria display filamentous structures. In yet other embodiments, said cyanobacteria were previously cultured in an aerated vessel. In yet other embodiments, said cyanobacteria were previously cultured in a non-aerated vessel.

In some embodiments of any of the above five aspects, said fermentative microorganisms have not been genetically modified to produce ethanol, butanol, or any alcohol. In some embodiments, said fermentative microorganisms have been genetically modified. In some embodiments, said fermentative microorganisms are Saccharomycetes or Schizosaccharomycetes. In some embodiments, said fermentative microorganisms are *Saccharamyces cerevisiae*. In some embodiments, said fermentative microorganisms are *Schizosaccharomyes pombe*. In some embodiments, said fermentative microorganisms are *Zymononas* or *Clostridium*. In some embodiments, said fermentative microorganisms are selected from the group consisting of: *Zymononas mobilis*, *Clostridium acetylbuttycum*, and *Clostridium beijerinckia*. In some embodiments, said cyanobacteria are members of the genus *Synechococcus, Trichodesmium*, or *Cyanothece*. In yet other embodiments, said fermentative microorganisms receive a substantial amount of their growth requirements from products released by said cyanobacteria. In some embodiments, said fermentative microorganisms are cultured in a vessel purged of oxygen. In some embodiments, said fermentative microorganisms are cultured in an aerated vessel. In some embodiments, said fermentative microorganisms are cultured in a non-aerated vessel. In some embodiments, said fermentative microorganisms are present at a concentration of $10^4$ to $10^{12}$ per mL in said medium.

In some embodiments of any of the above five aspects, said culture further comprises a fermentation product at a concentration of at least 0.01%, 0.02%, 0.03%, 0.04%, 0.05%, 0.06%, 0.07%, 0.08%, 0.09% 0.1%, 0.2%, 0.3%, 0.4%, 0.5%, 0.6%, 0.7%, 0.8%, 0.9%, 1.0%, 1.5%, 2.0%, 5.0%, 10%, 20%, 30%, 50%, or 70% (v/v). In some embodiments, said culture comprises a cyanobacteria:fermentative microorganism ratio of at least 1:1. In some embodiments, said cyanobacteria are removed from said first culture by centrifugation or filtration. In some embodiments, said cyanobacteria are removed from said first culture by a method selected from the group consisting of: counter-current membrane filtration, filtration, filtration with a pore filter, separation, decanting, a combination of separation and decanting, and microfiltration.

In some embodiments wherein a fermentation product is produced, the efficiency of the production of said fermentation product ranges from 0.1% to 50%. In some embodiments, the culture further comprises a fermentation product selected from the group consisting of: Acetic acid, Acetate, Acetone, 2,3-Butanediol, Butanol, Butyrate, $CO_2$, Ethanol, Formate, Glycolate, Lactate, Malate, Propionate, Pyruvate, Succinate. In yet other embodiments, the culture comprises butanol. In some embodiments, the culture comprises ethanol. In some embodiments the fermentation product is a biopolymer or biopolymer precursor.

In some embodiments of aspect five above, said growth requirements are one or more compounds selected from the group consisting of: sugars, inorganic nitrogen compounds, organic nitrogen compounds, and trace elements. In further embodiments, said fermentative microorganisms receive growth media from products released by said cyanobacteria and wherein said growth media is greater than 20%, 25%, 30%, 35%, 40%, 45%, 50%, 55%, 60%, 65%, 70%, 75%, 80%, 85%, 90% or 95% of the total growth requirements for said microorganisms. In further embodiments, said products released by said cyanobacteria are not the direct result of a genetic modification of said cyanobacteria.

In some embodiments of the first and second aspect, above, said salt concentration is greater than 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some embodiments of aspects three, four or five, the medium of said culture comprises a salt concentration greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%.

In some embodiments of aspects two, three, four or five, sugars, organic nitrogen compounds, inorganic nitrogen compounds, or trace elements in the medium of said culture are substantially derived from said cyanobacteria. In some embodiments, 50%, 60%, 70%, 80%, 90%, or 95% of one or more of said sugars, organic nitrogen compounds, inorganic nitrogen compounds or trace elements are substantially derived from said cyanobacteria.

In some embodiments of any of the above aspects, said culture medium comprises sea water. In some embodiments, said sea water is filtered sea water. In some embodiments, said culture occurs in a continuous culture system. In some embodiments, said culture is performed under anaerobic conditions.

In a sixth aspect, this disclosure provides a method of culturing microorganisms comprising: a. adding a population of fermentative microorganisms to a culture of cyanobacteria in order to obtain a microorganism co-culture, wherein the medium of said microorganism co-culture comprises a salt concentration greater than 1%; and b. culturing said microorganism co-culture under conditions to generate a fermentation product.

In a seventh aspect, this disclosure provides a method of culturing microorganisms comprising: a. adding a population of fermentative microorganisms selected from the group consisting of: Saccharomycetes, *Schizosaccharomyces* and fermentative bacteria, to a culture of cyanobacteria in order to obtain a microorganism co-culture; and b. culturing said microorganism co-culture under conditions to generate a fermentation product.

In an eighth aspect, this disclosure provides a method of culturing microorganisms comprising: a. removing cyanobacteria from a culture of cyanobacteria in order to obtain a feedstock medium substantially free of cyanobacteria; and b. culturing a population of fermentative microorganisms with said feedstock medium under conditions to generate a fermentation product.

In a ninth aspect, this disclosure provides a method of culturing microorganisms comprising: a. adding a population of fermentative microorganisms to a culture of cyanobacteria in order to obtain a microorganism co-culture; and b. culturing said microorganism co-culture under conditions to generate a fermentation product wherein said fermentative microorganisms receive growth media from products released by said cyanobacteria.

In some embodiments of aspects six, seven, eight or nine, said cyanobacteria are genetically modified to produce a fermentation product. In other embodiments, said cyanobacteria are genetically modified to produce ethanol, butanol, or any alcohol. In still further embodiments, said cyanobacteria comprise exogenous genes encoding pyruvate decarboxylase and alcohol dehydrogenase. In yet other embodiments, said cyanobacteria do not comprise exogenous genes encoding pyruvate decarboxylase and alcohol dehydrogenase. In still other embodiments, said cyanobacteria are cultured for greater than mid-log phase growth. In still other embodiments, the efficiency of the production of said fermentation product is from 1 to 50%. In yet other embodiments, said fermentative microorganisms are Saccharomycetes or Schizosaccharomycetes. In still other embodiments, said fermentative microorganisms are *Saccharamyces cerevisiae*. In some embodiments, said fermentative microorganisms are *Zymononas* or *Clostridium*. In some embodiments, said fermentative microorganisms are selected from the group consisting of: *Zymononas mobilis, Clostridium acetylbutrycum*, and *Clostridium beijerinckia*. In some embodiments, said cyanobacteria are members of the genus *Synechococcus* or *Trichodesmium*. In some embodiments, said cyanobacteria are previously cultured in a medium comprising sea water. In some embodiments, said cyanobacteria are previously cultured in a medium comprising filtered sea water. In some embodiments, said cyanobacteria of were previously cultured in the presence of solar energy. In some embodiments, said cyanobacteria were previously cultured under a light/dark regimen. In some embodiments, said cyanobacteria were previously cultured in the absence of solar energy. In some embodiments, said cyanobacteria were previously cultured for greater than 1, 5, 10, 15, 20, 25, 30, 40, 45, 50, 55, 60, 70, 75, 80, 90, 100, 150, or 200 days. In some embodiments, greater than 5%, 10%, 15%, 20%, 25% 30%, 35%, 40%, 45%, 50%, 55%, 60%, 65%, 70%, 75%, 80%, 85%, 90%, or 95% of said cyanobacteria are live organisms. In some embodiments, greater than 5%, 10%, 15%, 20%, 25% 30%, 35%, 40%, 45%, 50%, 55%, 60%, 65%, 70%, 75%, 80%, 85%, 90%, or 95% of said cyanobacteria display filamentous structures. In some embodiments, said cyanobacteria were previously cultured in an aerated vessel. In some embodiments, said cyanobacteria were previously cultured in a non-aerated vessel. In some embodiments, said fermentative microorganisms receive a substantial amount of their growth requirements from products released by said cyanobacteria. In some embodiments, the method further comprises culturing said fermentative microorganisms in a vessel purged of oxygen. In some embodiments, the method further comprises culturing said fermentative microorganisms in an aerated vessel.

In some embodiments, the method further comprises culturing said fermentative microorganisms in a non-aerated vessel. In some embodiments, said fermentation product is produced at a concentration of at least 0.01%, 0.02%, 0.03%, 0.04%, 0.05%, 0.06%, 0.07%, 0.08%, 0.09% 0.1%, 0.2%, 0.3%, 0.4%, 0.5%, 0.6%, 0.7%, 0.8%, 0.9%, 1.0%, 1.5%, 2.0%, 5.0%, 10%, 20%, 30%, 50%, or 70% (v/v). In some embodiments, said microorganism co-culture initially comprises a cyanobacteria:fermentative microorganism ratio of at least 1:1.

In some embodiments, said cyanobacteria are removed from said first culture by centrifugation or filtration. In some embodiments, said cyanobacteria are removed from said first culture by a method selected from the group consisting of: centrifugation, counter-current membrane filtration, filtration, filtration with a pore filter, separation, decanting, a combination of separation and decanting, and microfiltration. In some embodiments, the method further comprises culturing said fermentative microorganisms at a concentration of from $10^4$-$10^{12}$ cells/ml in said feedstock medium. In some embodiments, said growth media comprise one or more compounds selected from the group consisting of: sugars, inorganic nitrogen compounds, organic nitrogen compounds, and trace elements. In some embodiments, said growth media is greater than 20%, 25%, 30%, 35%, 40%, 45%, 50%, 55%, 60%, 65%, 70%, 75%, 80%, 85%, 90% or 95% of the total growth requirements for said microorganisms. In some embodiments, said products released by said cyanobacteria are not the direct result of a genetic modification of said cyanobacteria.

In some embodiments of the sixth aspect of the methods, said salt concentration is greater than 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%.

In some embodiments of the methods, the medium of said microorganism co-culture comprises a salt concentration greater than 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some embodiments, said culturing comprises culturing in a medium comprising a salt concentration greater than 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%.

In some embodiments, the method further comprises culturing in a medium comprising sea water, or comprising filtered sea water. In some embodiments, said culture comprises a medium comprising a fermentation product selected from the group consisting of: Acetic acid, Acetate, Acetone, 2,3-Butanediol, Butanol, Butyrate, $CO_2$, Ethanol, Formate, Glycolate, Lactate, Malate, Propionate, Pyruvate, Succinate. In some embodiments, said fermentation product is ethanol. In some embodiments, said fermentation product is butanol. In some embodiments, the fermentation product is a biopolymer or biopolymer precursor.

In some embodiments, the method further comprises the step of filtering the cultures to obtain a solution substantially free of microorganisms. In some embodiments, the method further comprises processing the cultures in order to produce a substantially-pure fermentation product; in some cases, said culturing is performed in a continuous culture system.

In some embodiments of the method, sugars, organic nitrogen compounds, inorganic nitrogen compounds, or trace elements in the medium of said microorganism co-culture are substantially derived from said cyanobacteria. In some embodiments of the method, sugars, organic nitrogen compounds, inorganic nitrogen compounds, or trace elements in the feedstock medium are substantially derived from said cyanobacteria. In some embodiments of the method, greater than 50%, 60%, 70%, 80%, 90%, or 95% of one or more of said sugars, organic nitrogen compounds or inorganic nitrogen compounds are substantially derived from said cyanobacteria.

In some embodiments of the method, the method further comprises culturing under anaerobic conditions. In still other embodiments, the method further comprises monitoring the growth rate of said fermentative organisms using a colorimeter equipped with a light filter.

INCORPORATION BY REFERENCE

All publications, patents, and patent applications mentioned in this specification are herein incorporated by reference in their entirety, to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Overview

Figure 1:
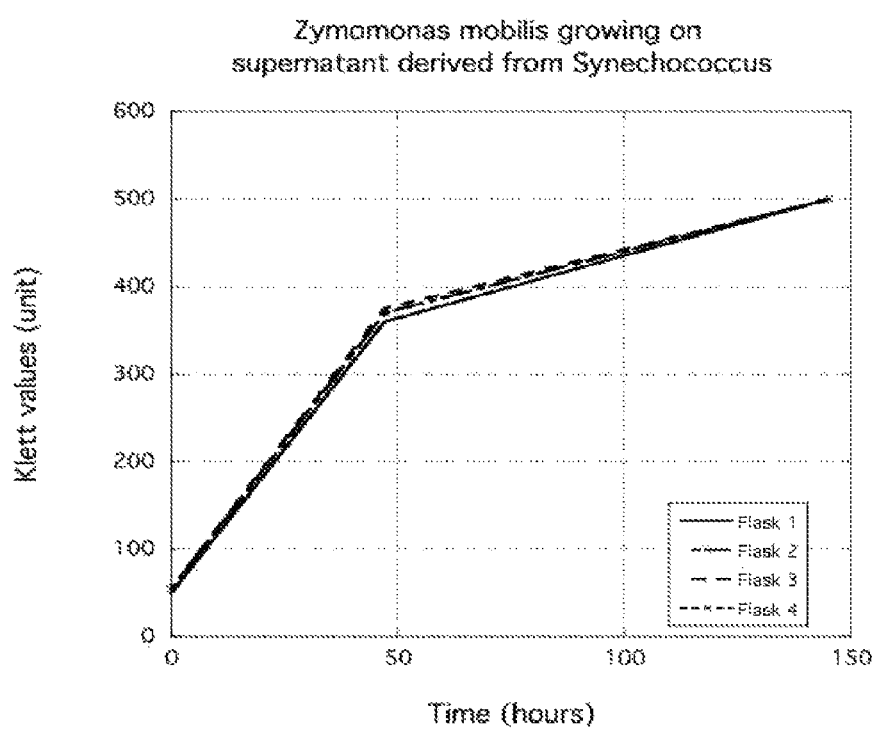
FIG. 1 is a graph that depicts the growth of *Z. mobilis* on centrifuged feedstock derived from *Synechococcus*.

This disclosure provides compositions of microorganisms as well as methods for culturing microorganisms. Also provided are mixtures, or co-cultures, of different microorganisms, especially mixtures of cyanobacteria with fermentative microorganisms. For example, cyanobacteria/yeast co-cultures are provided, as well as methods of culturing such co-cultures and methods of using such co-cultures. Also provided are feedstocks derived from cyanobacteria, as well as methods of producing feedstocks derived from cyanobacteria. This disclosure also provides methods of culturing fermentative organisms (e.g., yeast) in feedstock derived from cyanobacteria. In some embodiments, the culture medium for the cyanobacteria and/or fermentative organisms contains sea water, or other liquid with a high-salt concentration.

In general, the compositions and methods provided herein can be used in a wide range of applications. One salient application is the generation of fermentation products (e.g., ethanol, butanol, etc.) for use as biofuels and biopolymers. Other applications include the generation of fermentation products such as: bioisoprenes, such as those useful for production of rubber products; acrylics, such as those useful for production of paint and adhesives; adipic acids, such as those useful for production of nylon and plastics; and other bioproducts useful in production of soaps, oils, and personal care products. Still other applications include but are not limited to pharmaceutical products, food products, flavoring for foods, animal feeds, and aquaculture (e.g., shrimp food, fish food, etc.).

Microorganisms

The microorganisms provided herein include cultures of microorganisms and cultures that contain mixtures or consortia of different types of microorganisms. Cyanobacteria, also known as blue-green algae, blue-green bacteria, or cyanophyta, are a phylum (or division) of gram-negative bacteria that obtain their energy through photosynthesis. Cyanobacteria use chlorophyll-a as a primary light harvesting pigment and a bluish pigment, phycocyanin, as a secondary light harvesting pigment. However, different species may also exhibit different colors including light gold, yellow, brown, red, emerald green, blue, violet, and blue-black. (Raven et al., Biology of Plants, Fourth Edition, 183-185, (1986)). For example, some species express the phycoerythrin pigment, and exhibit a pink or red color. The light photons captured by pigments help drive the conversion of $CO_2$ and an electron donor (e.g., $H_2O$, $H_2S$) to carbohydrate. The photosynthetic reaction also produces oxygen and the oxidized product of the electron donor. Some types of cyanobacteria express the enzyme nitrogenase, and are capable of fixing nitrogen. Such cyanobacteria can convert atmospheric $N_2$ to ammonia, nitrate ($NO_3-$), nitrite ($NO_2-$), ammonium, urea and some amino acids.

Species of cyanobacteria may include, but are not limited to, *Spirulina* species, *Aphanizomenon* species, *Anabaena* species, *Aphanizomenon flos-aquae*, *Anabaena flos-aquae*, *Calothrix*, *Cylindrospermopsis*, *Cylindrospermum*, *Glocothece*, *Halotolerants*, *Leptolyngbya*, *Lyngbya*, *Micro cystis*/*Microcystis aeruginosa*, *Nodularia*, *Nostoc*, *Oscillatoria*/*Planktothrix*, *Phormidium*, *Prochlorococcus*, *Synechococcus*, *Synechocystis*, *Trichodesmium*, *Trichodesmium erythraeum*, and *Voronichinia*.

The cyanobacteria used in the present disclosure are preferably of the genus *Synechococcus*, *Trichodesmium*, and/or *Cyanothece*. In some embodiments, the cyanobacteria can be selected from, but are not limited to, one or more of the following cyanobacteria genera: Subsection I: *Aphanothece*, *Chamaesiphon*, *Chroococcus*, *Cyanobacterium*, *Cyanobium*, *Cyanothece*, *Dactylococcopsis*, *Gloeobacter*, *Gloeocapsa*, *Gloeothece*, *Microcystis*, *Prochlorococcus*, *Prochloron*, *Synechococcus*, *Synechocystis*, Subsection II: *Cyanocystis*, *Dermocarpella*, *Stanieria*, *Xenococcus*, *Chroococcidiopsis*, *Myxosarcina*, *Pleurocapsa*, Subsection III: *Arthrospira*, *Borzia*, *Crinalium*, *Geitlerinema*, *Halospirulina*, *Leptolyngbya*, *Limnothrix*, *Lyngbya*, *Microcoleus*, *Oscillatoria*, *Planktothrix*, *Prochlorothrix*, *Pseudanabaena*, *Spirulina*, *Starria*, *Symploca*, *Trichodesmium*, *Tychonema*, Subsection IV: *Anabaena*, *Anabaenopsis*, *Aphanizomenon*, *Calothrix*, *Cyanospira*, *Cylindrospermopsis*, *Cylindrospermum*, *Nodularia*, *Nostoc*, *Rivularia*, *Scytonema*, *Tolypothrix*, Subsection V: *Chlorogloeopsis*, *Fischerella*, *Geitleria*, *Iyengariella*, *Nostochopsis*, and *Stigonema*.

In some embodiments, the species of cyanobacteria may be selected from species adapted for survival under certain conditions (e.g., high or low temperatures, etc.). In another embodiment, the strain of cyanobacteria is selected from species that have been shown to naturally take up exogenous DNA, including but not limited to *Gloeocapsa alpicola*, *Agmenellum quadruplicatum*, *Anacystis nidulans*, *Synechocystis* sp. PCC 6803, and *Thermosynechococcus elongatus* BP-I. In another embodiment, the strain of cyanobacteria used is selected from species for which electroporation has been shown to be an effective method of introducing foreign DNA, including but not limited to *Anabaena* sp. M13 1, *Fremyella diplosiphon*, *Nostoc* PCC 7121, *Chroococcidiopsis* sp., *Spirulina platensis* C1, *Oscillatoria* MKU 277, and *Thermosynechococcus elongatus* BP-I.

Cyanobacteria include unicellular species and species that form colonies; colonies of cyanobacteria may also form filamentous structures, as well as sheets and hollow balls. In some cases, a percentage of the cyanobacteria of the present invention display filamentous structures. For example, about 5%, 10%, 15%, 20%, 25%, 30%, 35%, 40%, 45%, 50%, 55%, 60%, 65%, 70%, 75%, 80%, 85%, 90%, or 95% of the cyanobacteria of the present invention display filamentous structures. The terms "about" and "approximately," as used herein when referring to a measurable value, mean within 10% of a given value or range.

A percentage of the cyanobacteria in the present invention are live organisms. For example, greater than 5%, 10%, 15%, 20%, 25%, 30%, 35%, 40%, 45%, 50%, 55%, 60%, 65%, 70%, 75%, 80%, 85%, 90%, or 95% of cyanobacteria may be live organisms.

The compositions disclosed herein may comprise cyanobacteria and any known microorganism, however, preferably, the composition comprises cyanobacteria and one or more types of fermentative microorganisms. Examples of fermentative microorganisms include any known strain of yeast and any fermentative Bacteria, and Archaea. The compositions disclosed herein may also comprise isolated products secreted by cyanobacteria. Such products may be obtained by any method, including, but not limited to culturing the cyanobacteria for a length of time (as described herein), followed by a means to separate the cyanobacteria from the medium. The separated medium is thereby enriched with secretion products produced by the cyanobacteria. Means for separation may include, but are not limited to: centrifugation, countercurrent membrane filtration, filtration, filtration with a pore filter, separation, decanting, a combination of separation and decanting, microfiltration, and/or any combination of the foregoing.

As described herein, often the inventions of the present disclosure encompass a culture (or co-culture) comprising cyanobacteria and at least one fermentative microorganism. In some cases, the cyanobacteria in the culture may be homogenous. In other cases, the cyanobacteria are made up of a heterogenous population of different species. In some cases the fermentative microorganisms are homogenous; in other cases, they fermentative microorganisms are made up of a heterogenous population of different species. In some embodiments, the culture of the present invention contains cyanobacteria and at least one fermentative microorganism selected from the group consisting of: Saccharomycetes, Schizosaccharomyces and fermentative bacteria. In some embodiments, the culture of the present invention contains cyanobacteria and more than one fermentative microorganism selected from the group consisting of: Saccharomycetes, Schizosaccharomyces and fermentative bacteria. In still other embodiments, the culture of the present invention contains cyanobacteria and more than one fermentative microorganism described anywhere in the present disclosure. In yet other embodiments, the culture of the present invention contains at least one, or more than one, species of cyanobacteria and, at least one, or more than one, fermentative microorganism selected from the group consisting of: Saccharomycetes, *Schizosaccharomyces* and fermentative bacteria. In yet other embodiments, the culture of the present invention contains at least one, or more than one, species of cyanobacteria and, at least one, or more than one of any fermentative microorganism described herein.

In some embodiments, the culture of the present invention contains consortia or groups of cyanobacteria and/or yeast and/or bacteria and/or Archaea. In further embodiments, a consortia includes two or more distinct genera, species, or strains of cyanobacteria and/or yeast (and/or, e.g., bacteria, Archaea) chosen to specifically to, for example, improve resilience (e.g. to predation, competition, etc.), increase sugar production, increase bioproduct production (e.g., ethanol, butanol, etc.), and/or increase overall system productivity. In further embodiments, selected organisms may provide metabolites required by or consumed by other members of the consortia (e.g., fixed nitrogen, etc.). In various embodiments, consortia or groups of cyanobacteria and/or yeast include, by way of non-limiting examples: strains of *Synechococcus* and *Trichodesmium* such as CCMP 2669, CCMP1333, and CCMP 1985; strains of *Synechococcus*, *Trichodesmium*, and *Cyanothecae* such as *Cyanothece* sp. Miami BG043511; strains of *Synechococcus* and *Cyanothecae* such as *Cyanothece* sp. Miami BG043511; and multiple strains of *Synechococcus* such as PCC 7002 and CCMP 2669, and CCMP 1333, and *Synechococcus* sp. SF1 and CCMP 2669. In further embodiments, genera, species, or strains of cyanobacteria and/or yeast chosen for inclusion in cultured consortia or groups are obtained from a specific geographical region or location, or from a set of different geographical regions. Different geographical locations or regions may be positioned at different latitudinal gradients, for example. The geographical locations or regions may be located in a certain continent (e.g., North America, South America, Antarctica, Africa, Europe, Asia, or Australia, or, in a certain country (e.g., United States, etc.). The geographical locations or regions may be located in a specific area of a continent or country (e.g., western, eastern, northern, southern, south-western, south-eastern, north-western, northeastern, etc.). In some embodiments, genera, species, or strains of cyanobacteria and/or yeast chosen for inclusion in cultured consortia or groups are subjected to one or more of the natural selection and/or directed evolution processes described herein.

The yeast may be budding yeast (e.g., *Saccharamyces cerevisiae*) or fission yeast (e.g., *Schizosaccharomyces pombe*). The yeast may be in haploid or diploid forms. *S. cerevisiae* can grow aerobically on 6-carbon (hexose) sugars such as glucose, galactose and fructose, as well as disaccharides such as maltose, and trehalose, but fails to grow on lactose and cellobiose. The yeasts may be capable of undergoing fermentation under anaerobic conditions, aerobic conditions, or both anaerobic and aerobic conditions.

The ability of yeasts to use different sugars can differ depending on whether they are grown aerobically or anaerobically. All strains of yeast may use ammonia and urea as the sole nitrogen source, but cannot utilize nitrate since they lack the ability to reduce it to ammonium. Yeast, in general, can use most amino acids, small peptides and nitrogen bases as a nitrogen source. Amino acids of potential use as a nitrogen source for yeast include but are not limited to: alanine, arginine, aspartic acid, asparagine, glutamic acid, glutamine, methionine, isoleucine, leucine, phenylalanine, proline, serine, threonine, tryptophan, tyrosine, and valine. Histidine, glycine, cystine and lysine are, however, not readily utilized.

Yeasts also generally may have a requirement for phosphorus, which is assimilated as a dihydrogen phosphate ion, and sulfur, which can be assimilated as a sulfate ion or as organic sulfur compounds like the amino acids methionine and cysteine. Some metals such as magnesium, iron, calcium, and zinc also may enhance yeast growth. Examples of types of yeast encompassed by the present disclosure include but are not limited to: Saccharomycetes, *Saccharomyces*, *Schizosaccharomyces*, *Schizosaccharomycetes*, *Saccharamyces cerevisiae*, *Schizosaccharomyes pombe*, and *Saccharomyces bayanus*. In some cases, this disclosure provides cultures comprising at least one fermentative microorganism selected from the group consisting of Saccharomycetes, *Saccharomyces*, *Schizosaccharomyces*, or any combination thereof.

This disclosure also includes any species of the genus *Saccharomyces*, including, but not limited to: *Saccharomyces boulardii*, *Saccharomyces bulderi*, *Saccharomyces cariocanus*, *Saccharomyces cariocus*, *Saccharomyces cerevisiae*, *Saccharomyces chevalieri*, *Saccharomyces dairenensis*, *Saccharomyces ellipsoideus*, *Saccharomyces martiniae*, *Saccharomyces monacensis*, *Saccharomyces norbensis*, *Saccharomyces paradoxus*, *Saccharomyces pastorianus*, *Saccharomyces spencerorum*, *Saccharomyces turicensis*, *Saccharomyces unisporus*, *Saccharomyces uvarum*, and *Saccharomyces zonatus*. This disclosure also includes any species of *Schizosaccharomyces* including but not limited to *S. japonicus*, *S. kambucha*, *S. octosporus*, and *S. pombe*.

Additional fermentative organisms that can be used in the present disclosure include any fermentative bacteria, including bacteria of the genus *Zymomonas* or of the genus *Clostridium*. Members of *Zymomonas* genus are gram negative, anaerobic, non-sporulating, polarly-flagellated, rod-shaped bacteria. A non limiting example of a species of *Zymomonas* bacteria of particular use in the present invention is *Zymomonas mobilis*.

The *Clostridium* genus encompasses rod-shaped, gram-positive bacteria that are obligate anaerobes and capable of producing endospores. Preferably, the *Clostridium* bacteria of the present invention are of the species *Clostridium acetylbutyricum* or *Clostridium beijerinckia*. However, any species of *Clostridium* is potentially of use in the present invention including but not limited to: *Clostridium phytofermentans*, *thermocellum*, *Clostridium beijerinickii*, *Clostridium tyrobutyricum*, *Clostridium thermobutyricum*, *Clostridium acetobutylicum*, *Clostridium aerotolerans*, *Clostridium baratii*, *Clostridium bifermentans*, *Clostridium botulinum*, *Clostridium difficile*, *Clostridium tyrobutyricum*, *Clostridium cadaveris*, *Clostridium chauvoei*, *Clostridium clostridioforme*, *Clostridium colicanis*, *Clostridium fallax*, *Clostridium feseri*, *Clostridium formicaceticum*, *Clostridium histolyticum*, *Clostridium innocuum*, *Clostridium kluyveri*, *Clostridium ljungdahli*, *Clostridium laramie*, *Clostridium lavalens*, *Clostridium nigrificans*, *Clostridium novyi*, *Clostridium oedematiens*, *Clostridium paraputrificum*, *Clostridium perfringens*, *Clostridium phytofermentans*, *Clostridium piliforme*, *Clostridium ramosum*, *Clostridium scatologenes*, *Clostridium septicum*, *Clostridium sordellii*, *Clostridium sporogenes*, *Clostridium tertium*, *Clostridium tetani*, *Clostridium thermocellum*, *Clostridium thermosaccharolyticum*, and *Clostridium beijerickii*.

In addition, any other fermentative bacteria may be used in the present invention. For example, *E. coli* are rod-shaped, gram-negative, facultative anaerobic, non-sporulating bacteria. Some types of genetically-modified *E. coli* are capable of producing fermentation products such as ethanol under anaerobic conditions.

Cyanobacteria capable of surviving and growing in medium containing a fermentative product, e.g. ethanol, butanol, may be especially useful in the provided inventions. For example, in some embodiments, a cyanobacteria species that is able to grow in medium containing a fermentative product (e.g., at least 3% EtOH) is used. In other cases, the cyanobacteria species is able to grow in medium that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95% EtOH or other fermentative product.

Other potential fermentative microorganisms of use in the present disclosure include but are not limited to: *Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis*, and *Bacillus subtilis*.

A percentage of the fermentative microorganisms in the present invention are live organisms. For example, greater than 5%, 10%, 15%, 20%, 25%, 30%, 35%, 40%, 45%, 50%, 55%, 60%, 65%, 70%, 75%, 80%, 85%, 90%, or 95% of the fermentative microorganisms may be live organisms.

The disclosure provides microorganisms that are obligate anaerobes, which cannot use oxygen for growth and are harmed by it; aerotolerant organisms, which cannot use oxygen for growth, but tolerate the presence of it; and/or facultative anaerobes, which can grow without oxygen but can utilize oxygen if it is present. This disclosure also provides cultures comprising any combination of the foregoing.

The microorganisms of the present disclosure often exist in nature originally. For example, cyanobacteria may be present in sea water at a concentration of greater than 1, 2, 5, 10, $10^2$, $10^3$, $10^4$, $10^5$, $10^6$, $10^7$, $10^8$, $10^9$, $10^{10}$, $10^{11}$, $10^{12}$, $10^{13}$, or $10^{14}$ cells/ml. In some embodiments, the microorganisms of the present disclosure are cultured at a particular concentration. For example, the cyanobacteria and/or fermentative microorganisms may be present in a culture at a concentration of greater than 1, 2, 5, 10, $10^2$, $10^3$, $10^4$, $10^5$, $10^6$, $10^7$, $10^8$, $10^9 10^{10}$, $10^{11}$, $10^{12}$, $10^{13}$ or $10^{14}$ cells/ml. In some embodiments, the cyanobacteria and/or fermentative microorganisms are cultured for greater than mid-log phase growth. In some embodiments, the cyanobacteria and/or fermentative microorganisms are cultured for greater than 1, 5, 10, 15, 20, 25, 30, 40, 45, 50, 55, 60, 70, 75, 80, 90, 100, 150, or 200 days.

The microorganisms (e.g., cyanobacteria, yeast, fermentative bacteria, Archaea, etc.) of the present disclosure, in some embodiments, are grown from isolates obtained from nature (e.g., wild-types) in geographically-specific sites. In further embodiments, wild-type strains are subjected to natural selection to enhance desired traits (e.g., tolerance of certain environmental conditions such as temperature, salt concentration, pH, oxygen concentration, EtOH concentration, nitrogen concentration, etc.). For example, a wild-type strain (e.g., yeast) is selected for its ability to grow and/or ferment in a culture of a specific salt solution, e.g., 3 to 4% NaCl). In other embodiments, wild-type strains are subjected to directed evolution to enhance desired traits (e.g., sugar production, salt tolerance, bioproduct formation, etc.). In some embodiments, the cultures of microorganisms are obtained from culture collections exhibiting desired traits. In further embodiments, strains selected from culture collections are further subjected to directed evolution and/or natural selection in the laboratory. In some preferred embodiments, cyanobacteria (or other fermentative organisms) are subjected to directed evolution and selection for a specific property (e.g., rate of sugar production), while yeast are subjected to natural selection to enhance a specific a property (e.g., salt tolerance). The natural selection of yeast may be for any number of properties, including, but not limited to: growth rate at a particular salinity, fermentation production at a particular salinity. In some embodiments, the cyanobacteria (or other microorganism) and/or yeast (or other fermentative microorganism) is selected for its ability to survive a range of salinities. In some cases, the cyanobacteria of the present disclosure are able to survive in medium with a relatively low salinity (e.g., about or equal to 0.3%, 0.4%, 0.5%, 0.6%, 0.7%, 0.8%. 0.9%, 1.0% salt concentration).

In some cases, the cyanobacteria of the present disclosure are able to survive even after being subjected to increased or decreased salinity, or fluctuations of salinity. For example, cyanobacteria of the present disclosure are cultured in sea water and then survive after the sea water undergoes a decrease in salt concentration. In some cases, cyanobacteria of the present disclosure are cultured in sea water and then survive after the sea water undergoes an increase in salt concentration. In some cases, such fluctuations in salinity are rapid, for example a 2-fold, 3-fold, 4-fold, or 5-fold change in salinity (either increase or decrease) that occurs over a short period of time (e.g., 1-5 hours).

In light of the disclosure provided herein, those of skill in the art will recognize that directed evolution generally involves three steps. The first step is diversification, wherein the population of organisms is diversified by increasing the rate of random mutation creating a large library of gene variants. Mutagenesis can be accomplished by methods known in the art (e.g., chemical, ultraviolet light, etc.). The second step is selection, wherein the library is tested for the presence of mutants (variants) possessing the desired property using a screening method. Screens enable identification and isolation of high-performing mutants. The third step is amplification, wherein the variants identified in the screen are replicated. These three steps constitute a "round" of directed evolution. In some embodiments, the microorganisms of the present disclosure are subjected to a single round of directed evolution. In other embodiments, the microorganisms of the present disclosure are subjected to multiple rounds of directed evolution. In various embodiments, the microorganisms of the present disclosure are subjected to 2, 3, 4, 5, 6, 7, 8, 9, 10, 20, 30, 40, 50, 60, 70, 80, 90, or 100 or more rounds of directed evolution. In each round, the organisms expressing the highest level of the desired trait of the previous round are diversified in the next round to create a new library. This process may be repeated until the desired trait is expressed at the desired level.

The cyanobacteria may be generated by a process of directed evolution. In some cases, a strain of cyanobacteria used in the inventions of the disclosure is generated from directed evolution to select for a strain that tolerates a certain environment condition (e.g., temperature, salt concentration, pH, oxygen concentration, EtOH concentration, nitrogen concentration, etc.). In some cases, a strain of cyanobacteria used in the inventions of the disclosure is generated from directed evolution to select for a strain that tolerates higher concentrations of ethanol. An approach to selecting such a strain is to grow cyanobacteria cultures in increasing levels of ethanol, and then to amplify surviving organisms.

The methods and compositions described herein (e.g., the methods of directed evolution) may increase the rate of sugar production by cyanobacteria, or other organisms. Often, the increase in rate of sugar production is by more than 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 50, 75, or 100-fold over the original rate (e.g., rate of the wild-type organism or rate of the starting organism) of the sugar production for the cyanobacteria, or other organism. Similarly, the methods and compositions described herein may increase the total quantity of sugar production by cyanobacteria or other organisms, over a period of time. For example, the increase in quantity of sugar produced may be greater than 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 50, 75, or 100-fold over a specified time period, when compared to the quantity of sugar produced by the original (e.g., wild-type organism, starting organism) over the same time period.

In some examples, cyanobacteria, which normally secrete sugars at the rate of approximately 2% (w/v) per 24 hours (e.g., 20 grams sugar per liter of solution per day), are made to secrete sugars at an increased rate. The cyanobacteria are subjected to conditions to enable the cyanobacteria to produce sufficient quantities of sugar to support yeast growth, fermentation, and ethanol production by application of the techniques and processes described herein. In further cases, cyanobacteria subjected to the techniques and processes described herein secrete sugars at the rate of 2%, 4%, 6%, 8%, 10%, 12%, 14%, 16%, 18%, or 20% (w/v), or more, per 24 hours. In further examples, sugar producing cyanobacteria cultures include $10^2$, $10^3$, $10^4$, $10^5$, $10^6$, $10^7$, $10^8$, $10^9$, $10^{10}$, $10^{11}$, $10^{12}$, $10^{13}$, or $10^{14}$ cyanobacteria cells/ml. In still further embodiments, sugar producing cyanobacteria cultures include $10^4$ to $10^9$ cyanobacteria cells/ml.

The cyanobacteria of the present disclosure may be genetically modified, while in other cases, the cyanobacteria of the present disclosure are not genetically modified. Similarly, the fermentative microorganisms of the present disclosure may be genetically modified, while in other cases, the fermentative microorganisms are not genetically modified. In some cases, the cyanobacteria are a mixture of genetically modified and wild-type microorganisms. In some cases, the fermentative microorganisms are a mixture of genetically-modified and wild-type microorganisms. As described further herein, at times the present invention comprises both wild-type cyanobacteria and wild-type fermentative microorganisms; wild-type cyanobacteria and genetically-modified fermentative microorganisms; genetically-modified cyanobacteria and wild-type fermentative microorganisms; or genetically-modified cyanobacteria and genetically-modified fermentative microorganisms. Also described further herein, at times the present invention comprises cyanobacteria and/or fermentative microorganisms that have been subjected to natural selection and/or directed evolution. In some cases, the cyanobacteria are a mixture of microorganisms modified by natural selection and/or directed evolution and wild-type microorganisms. In some cases, the cyanobacteria are a mixture of microorganisms modified by natural selection and/or directed evolution and microorganisms genetically-modified by other methods disclosed herein. In some cases, the fermentative microorganisms are a mixture of microorganisms modified by natural selection and/or directed evolution and wild-type microorganisms. In some cases, the fermentative microorganisms are a mixture of microorganisms modified by natural selection and/or directed evolution and microorganisms genetically-modified by other methods disclosed herein.

Some Examples of Genetic Modifications and Other Features of Microorganisms

The cyanobacteria and/or fermentative microorganisms can be genetically modified by any method known in the art (e.g., transfection, electroporation, etc.). The genetic modifications may also be of any type known in the art. The genetic modification may be directly or indirectly related to the production of a fermentation product, e.g., ethanol or butanol. The genetic modification may also have no relation to the generation of a fermentation product, or only a very attenuated relationship to the generation of a fermentation product. In some cases, the genetic modification may be directly or indirectly related to the production of a fermentable product, e.g., sugar. The genetic modification may also have no relation to the generation of a fermentable product, or only a very attenuated relationship to the generation of a fermentable product.

In some examples, the cyanobacteria are genetically modified to provide a particular nutrient that can be metabolized by the fermentative microorganism of the particular embodiment of the invention. In some examples, the cyanobacteria may already produce the nutrient, but are genetically-modified to produce enhanced amounts of nutrients.

The cyanobacteria or fermentative microorganisms may be genetically modified to produce a fermentation product. For example, the cyanobacteria and/or fermentative microorganisms are genetically modified to produce, or improve production of, ethanol, butanol, or any alcohol or other fermentation product described herein. In some cases, the cyanobacteria and/or fermentative microorganisms are genetically modified by the addition of one or more exogenous (or heterologous) genes encoding pyruvate decarboxylase and/or alcohol dehydrogenase. Non-limiting examples of other possible genes that could be introduced to the cyanobacteria and/or fermentative microorganisms include but are not limited to: pyruvate dehydrogenase, pyruvate decarboxylase, alcohol dehydrogenase, pyruvate formate lysase, formate hydrogen lysase, formate dehydrogenase, or any mixture or combination thereof. Further descriptions of potential genetic modifications can be found in the art, see, e.g., Dellomonaco et al., (2010) *Microbial Cell Factories,* 9:3, http://www.microbialcellfactories.com/content/9/1/3.

The cyanobacteria and/or fermentative microorganisms disclosed herein may be genetically-modified in order to regulate fermentative biochemical pathways, express saccharolytic enzymes, or to increase tolerance to environmental conditions (e.g., temperature, salt concentration, pH, oxygen concentration, EtOH concentration, nitrogen concentration, etc.) during fermentation.

In some embodiments, the cyanobacteria and/or fermentative microorganisms are halophilic microbes. In some embodiments, the cyanobacteria and/or fermentative microorganisms are either naturally suited for, selected for, or genetically modified, to thrive in media with salt concentrations greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%.

In some examples, the cyanobacteria are genetically modified to produce, or improve production of a nutrient (e.g., sugar, nitrogen compound, trace element) that is consumed by the fermentative microorganism. For example, if the fermentative microorganism metabolizes (or catabolizes) six-carbon sugars, the cyanobacteria may be genetically modified to produce glucose. In some examples, the fermentative microorganisms are genetically modified to catabolize a nutrient (e.g., sugar, nitrogen compound, trace element) that is secreted by cyanobacteria, or genetically-modified cyanobacteria. For example, if the cyanobacteria secrete a specific nitrogen compound, the fermentative microorganism may be genetically engineered to catabolize that specific nitrogen compound.

In some cases, the cyanobacteria and/or fermentative microorganisms are genetically-modified in any other manner known in the art. For example, they may be genetically modified to express a fluorescent protein, e.g., green fluorescent protein, red fluorescent protein. In other cases, they may be genetically modified to tolerate a particular type of environment (e.g., high temperature). In still other cases, they may be genetically modified to tolerate high-salt concentrations. In some cases, they may not be genetically modified to tolerate high-salt concentrations. For example, in some cases the cyanobacteria and/or fermentative microorganisms are genetically-modified to express a gene for salt tolerance (e.g., the HAL1 yeast gene). In some embodiments, the cyanobacteria and/or fermentative microorganisms are not genetically-modified to express a gene for salt tolerance (e.g., HAL1 yeast gene).

In some embodiments, the modifications to the microorganisms may result in regulation of fermentative biochemical pathways, expression of certain genes (e.g., genes encoding saccharolytic enzymes), or increased tolerance to environmental conditions during fermentation. Cyanobacteria or fermentative organisms described herein may be transformed with heterologous polynucleotides encoding one or more genes for the pathway, enzyme, or protein of interest. In another embodiment, cyanobacteria or fermentative organisms are transformed to produce multiple copies of one or more genes for the pathway, enzyme, or protein of interest. In one embodiment, Cyanobacteria or fermentative organisms described herein are transformed with heterologous polynucleotides encoding one or more enzymes for the hydrolysis and/or fermentation of a hexose. As a result, said cyanobacteria or fermentative microorganism may have the improved ability to produce ethanol (e.g., improved productivity levels or yields) compared to cyanobacteria or fermentative microorganisms that are not transformed.

Other genetic modifications can be made to enhance the ethanol production. For example, the host can further comprise an additional heterologous DNA segment, the expression product of which is a protein involved in the transport of mono- and/or oligosaccharides into the recombinant host. Likewise, additional genes from the glycolytic pathway can be incorporated into the host to redirect the bioenergetics of the ethanolic production pathways. In such ways, an enhanced rate of ethanol production can be achieved.

In order to improve the production of biofuels (e.g. ethanol, butanol), modifications can be made in transcriptional regulators, genes for the formation of organic acids, carbohydrate transporter genes, genes that influence the formation/regenerate of enzymatic cofactors, genes that influence ethanol tolerance, genes that influence salt tolerance, genes that influence growth rate, genes that influence oxygen tolerance, genes that influence catabolite repression, genes that influence hydrogen production, genes that influence resistance to heavy metals, genes that influence resistance to acids or genes that influence resistance to aldehydes.

Those skilled in the art will appreciate that a number of modifications can be made to the methods exemplified herein. For example, a variety of promoters can be utilized to drive expression of the heterologous genes in cyanobacteria and/or fermentative microorganisms described herein. The skilled artisan, having the benefit of the instant disclosure, will be able to readily choose and utilize any one of the various promoters available for this purpose. Similarly, skilled artisans can utilize a higher copy number plasmid. In another embodiment, constructs can be prepared for chromosomal integration of the desired genes. Chromosomal integration of foreign genes can offer several advantages over plasmid-based constructions, the latter having certain limitations for commercial processes. Ethanologenic genes have been integrated chromosomally in $E.$ $coli$ B; see Ohta et al. (1991) Appl. Environ. Microbiol. 57:893-900. In general, this is accomplished by purification of a DNA fragment containing (1) the desired genes upstream from an antibiotic resistance gene and (2) a fragment of homologous DNA from the target organism. This DNA can be ligated to form circles without replicons and used for transformation.

Microorganism Cultures

In some embodiments, a composition of the invention comprises both microorganisms and a particular culture medium. In some cases, one or more microorganisms is cultured in one type of medium first and then transferred to a different type of medium. For example, one or more fermentative organisms described herein may be cultured in a specific medium and then transferred to medium comprising cyanobacteria, or products (or nutrients) secreted by cyanobacteria. Similarly, the cyanobacteria described herein may be cultured in a specific culture medium and then transferred to a different medium. In some cases, the medium used for the cyanobacteria/fermentative microorganism co-culture is the same medium that was previously used to culture the cyanobacteria and/or the fermentative microorganisms in the culture. In some cases, the medium used for the cyanobacteria/fermentative microorganism co-culture is different from the culture medium previously used to culture the cyanobacteria and/or the fermentative microorganisms.

In many embodiments of the instant disclosure, the culture (or co-culture) medium contains a specific salt concentration. In some cases, the salt concentration is high, but the salt concentration may also be none, low, or moderate. In some cases, the salt concentration of the culture or (co-culture) medium herein is greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some cases, the salt concentration of the culture or (co-culture) medium herein is sea water or filtered seawater. In some embodiments, the fermentative microorganisms described herein are cultured in a medium with a salt concentration greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some embodiments, the fermentative microorganisms described herein are cultured in sea water or filtered sea water. In some embodiments, the cyanobacteria described herein are cultured in a medium with a salt concentration greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some embodiments, the cyanobacteria described herein are cultured in sea water or filtered sea water. In some embodiments, the method comprises culturing cyanobacteria described herein (or other microorganism or co-culture of microorganisms) in the presence of sea water, but in the absence of any fresh water, or in the absence of a substantial amount of fresh water (e.g., less than 5%, 10%, 20%, 30%, 40%, or %50) of the total culture medium is made up of water that was originally fresh water).

An advantage of many of the embodiments of the current disclosure is that the cyanobacteria need not be grown on defined medium. Instead, the cyanobacteria may be grown on sea water or filtered sea water. In some embodiments, the sea water or filtered sea water is monitored for input seawater parameters (e.g., PO$_4$, trace elements, salts, temperature, pH, etc.). In further embodiments, growth conditions are managed by specific adjustment of individual parameters falling outside specific ranges. In some embodiments, the sea water or filtered sea water is monitored for one or more organisms of interest (e.g., cyanobacteria, predators, competitors, etc.). In further embodiments, growth conditions are managed by adjustment of the concentration and/or presence of one or more particular organisms of interest. In some embodiments, the sea water or filtered sea water may be supplemented with other components, including any component listed in Table 1. In some embodiments, it may be useful to grow the cyanobacteria for a certain amount of time on defined medium. For such embodiments, the cyanobacteria may be grown on A+medium. The ingredients to prepare A+medium are provided in Table 1.

TABLE 1

A + Medium

| Chemical component: | g/L |
|---|---|
| NaCl | 18 |
| MgSO$_4$•7H$_2$O | 5.0 |
| NaNO$_3$ | 1.0 |
| KCl | 0.6 |

| Stock Solutions: | ml/L |
|---|---|
| KH$_2$PO$_4$ (50 g/L) | 1.0 |
| CaCl$_2$ (37 g/L) | 7.2 |
| Na EDTA (3 g/L) | 10.0 |
| FeCl$_3$•6H$_2$O (3.89 g/L with 0.1N HCL) | 1.0 |
| TRIS (100 g/L adjust to pH 8) | 10.0 |
| P1 Trace Metal solution: | 1.0 ml/L |
| H$_3$BO$_3$ | 34.26 g/L |
| MnCl$_2$•4H$_2$O | 4.32 g/L |
| ZnCl$_2$ | 0.315 g/L |
| MoO$_3$ | 0.039 g/L |
| CuSO$_4$•5H$_2$O | 0.003 g/L |
| CoCl$_2$•6H$_2$O | 0.01215 g/L |
| Distilled H$_2$O | Fill to 1 L |

In some embodiments, stock solutions and PI trace elements indicated in Table 1 are prepared. The chemical components are added to ca. 700 ml distilled water on a stir plate. Each component is dissolved before adding the next component. The stock solutions are then added to the media, followed by adding 1.0 ml PI trace metal solution to the media. The volume is then brought up to 1.0 L with distilled H$_2$O. In some embodiments, the media is autoclaved (121° C. for 20 min.) or filter sterilized with a 0.2 micron filter. 100 µL Vitamin B12 solution is then added to cooled or filtered media. To make the stock solution for Vitamin B12: 1 mg Vitamin B12 is added to 1000 ml distilled water, filter sterilized (0.2 µM), and stored covered with foil in refrigeration.

An advantage of many of the embodiments of the current disclosure is that the fermentative microorganisms described herein need not be grown on defined medium. Instead, the fermentative microorganisms may be grown on a medium supplemented with nutrients, catabolites, or other substances released or produced by cyanobacteria. In some cases, it may be helpful to grow the fermentative microorganisms on defined medium, or to supplement the medium for fermentative microorganisms with one or more substances derived from a medium for fermentative microorganisms. An example of the components of medium for *Zymomonas mobilis* is the ATCC #948 medium shown in Table 2. The medium for the *Zymomonas mobilis* (e.g., ATCC #948) may be subsequently autoclaved after preparation, such as at 121° C. for about 20 or more minutes. Similarly, an example of the components of medium for yeast, e.g., *S. cerevisiae* is provided in Table 3, which provides the ingredients for YEPD medium. In order to produce solid medium, 1.5% agar is added to the solution. The YEPD medium may be may be subsequently autoclaved, such as at 121° C. for about 20 or more minutes.

TABLE 2

ATCC #948 media

| Component | g/L |
|---|---|
| Glucose | 20 |
| Yeast Extract | 5 |
| Distilled H$_2$O | Fill to 1 L |

TABLE 3

YEPD media

| Component | g/L |
|---|---|
| Peptone | 10 |
| Dextrose | 10 |
| Yeast Extract | 20 |
| Distilled H$_2$O | Fill to 1 L |

In some cases, the cyanobacteria are previously cultured in a medium with a certain salt concentration and then either the medium alone, the cyanobacteria alone, or the medium in combination with the cyanobacteria are cultured with fermentative microorganisms. For example, the cyanobacteria may be cultured in a medium with a salt concentration of greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30% prior to being co-cultured with the fermentative microorganisms described herein. The cyanobacteria may be cultured in sea water or filtered sea water prior to being co-cultured with the fermentative microorganisms described herein. In some cases, the cyanobacteria (or other microorganism) is co-cultured with yeast (or other fermentative microorganisms) throughout all of, or a portion of, a fermentation process. For example, the cyanobacteria are co-cultured with yeast while the yeast produce EtOH.

In still other cases, the cyanobacteria are cultured in a medium with a salt concentration of greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%; and then feedstock is produced by completely or substantially removing the cyanobacteria from the medium, as described herein. A composition provided herein may include the foregoing feedstock and one or more fermentative microorganism described herein. In still other cases, the cyanobacteria are cultured in sea water or filtered sea water, and then feedstock is produced by completely or substantially removing the cyanobacteria from the medium. A composition provided herein may include the foregoing feedstock and one or more fermentative microorganism described herein.

In some cases, the fermentative organisms are cultured in a medium with a salt concentration of greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some cases, the fermentative organisms are cultured in sea water or filtered seawater. In some cases, the fermentative organisms are cultured in any manner and then transferred to a medium with a salt concentration of greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some cases, the fermentative organisms are cultured in any manner and then transferred to a medium containing sea water or filtered seawater.

In some embodiments, the fermentative microorganisms receive a substantial amount of growth media (e.g., nutrients, catabolites) from products released by the cyanobacteria. In some cases, the fermentative microorganisms receive at least 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, 30%, 35%, 40%, 45%, 50%, 55%, 60%, 65%, 70%, 75%, 80%, 85%, 90%, 95%, or 100% of their maximum growth requirements for a particular nutrient (e.g., sugar, nitrogen compound) from products released by cyanobacteria.

In some cases, a microorganism co-culture provided herein has a cyanobacteria:fermentative microorganism ratio of at least $10^5:1$, $10^4:1$, $10^3:1$, 100:1, 90:1, 80:1, 85:1, 80:1, 75:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50, 1:75, 1:80, 1:85, 1:90, 1:100, $1:10^2$, $1:10^3$, $1:10^4$, or $1:10^5$. In some cases, the foregoing ratio refers to the total cyanobacteria and/or fermentative microorganisms in a culture. In some cases, the foregoing ratio refers to a specific strain of cyanobacteria and/or fermentative microorganism in a culture.

In some embodiments, the cyanobacteria and/or fermentative microorganism cultures (or co-cultures) are cultured for greater than 1, 5, 10, 15, 20, 25, 30, 40, 45, 50, 55, 60, 70, 75, 80, 90, 100, 150, or 200 days. In some embodiments, the cyanobacteria and/or fermentative microorganism cultures (or co-cultures) are cultured until they reach greater than mid-log phase growth.

In some embodiments, the cyanobacteria and/or fermentative microorganism cultures (or co-cultures) are cultured under a light/dark regime. In some cases, the light/dark regime may be cycles wherein the cultures are cultured under light conditions for a certain amount of hours, followed by culture under dark conditions for a certain amount of hours. For example, a light/dark cycle could be a range of hours of light:hours of dark, such as 8:16, 9:15, 10:14, 11:13, 12:12, 13:11, 14:10, 15:9, or 16:8. Repeated light/dark cycles may be conducted over a period of time, such as a period of time greater than 1, 5, 10, 15, 20, 25, 30, 40, 45, 50, 55, 60, 70, 75, 80, 90, 100, 150, or 200 days. In some cases, the light phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours. In some cases, the dark phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours.

In some embodiments, the cyanobacteria and/or fermentative microorganism cultures (or co-cultures) are cultured in the presence of solar energy. As used herein, the term "solar energy" includes natural sunlight, and may include direct sunlight and indirect sunlight. In some embodiments, the cyanobacteria and/or fermentative microorganism cultures (or co-cultures) are cultured in the presence of artificial light (e.g., 150 W halogen light). In some embodiments, the cyanobacteria and/or fermentative microorganism cultures (or co-cultures) are cultured in the absence of solar energy. In some embodiments, the cyanobacteria and/or fermentative microorganism cultures (or co-cultures) are cultured in an aerated vessel. In some embodiments, the cyanobacteria and/or fermentative microorganism cultures (or co-cultures) are cultured in a non-aerated vessel or under anaerobic conditions. In some embodiments, the cyanobacteria and/or fermentative microorganism cultures (or co-cultures) are cultured in a vessel purged of oxygen. In some embodiments, the cyanobacteria and/or fermentative microorganism cultures (or co-cultures) are cultured in a vessel purged of nitrogen. In some embodiments, the cyanobacteria and/or fermentative microorganism cultures (or co-cultures) are cultured in a culture medium that comprises a fermentation product at a concentration of at least 0.1%, 0.3%, 0.5%, 0.6%, 1.0%, 1.5%, 2.0%, 5.0%, 10%, 20%, 30%, 50%, or 70% (v/v). In some embodiments, the cyanobacteria and/or fermentative microorganism cultures (or co-cultures) are able to fix nitrogen. Thus, in some embodiments, the cyanobacteria and/or fermentative microorganism cultures (or co-cultures) do not require the addition of fertilizers that comprise nitrogen. In some embodiments, the cultures or co-cultures grow in the absence of exogenous nitrogen, other than atmospheric nitrogen.

In some embodiments, the cyanobacteria and/or fermentative microorganism cultures (or co-cultures) are cultured for greater than 1, 5, 10, 15, 20, 25, 30, 40, 45, 50, 55, 60, 70, 75, 80, 90, 100, 150, or 200 days. In some embodiments, the cyanobacteria and/or fermentative microorganism cultures (or co-cultures) are cultured until they reach greater than mid-log phase growth.

In some embodiments, prior to being mixed with the fermentative microorganism cultures, the cyanobacteria are cultured under a light/dark regime. In some cases, the light/dark regime may be cycles wherein the cultures are cultured under light conditions for a certain amount of hours, followed by culture under dark conditions for a certain amount of hours. For example, a light/dark cycle could be 1a range of hours of light:hours of dark, such as 8:16, 9:15, 10:14, 11:13, 12:12, 13:11, 14:10, 15:9, or 16:8. Repeated light/dark cycles may be conducted over a period of time, such as a period of time greater than 1, 5, 10, 15, 20, 25, 30, 40, 45, 50, 55, 60, 70, 75, 80, 90, 100, 150, or 200 days. In some cases, the light phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours. In some cases, the dark phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours.

In some embodiments, prior to being mixed with the fermentative microorganism cultures, the cyanobacteria are cultured in the presence of solar energy. In some embodiments, prior to being mixed with the fermentative microorganism cultures, the cyanobacteria are cultured in the presence of artificial light (e.g., 150 W halogen light). In some embodiments, prior to being mixed with the fermentative microorganism cultures, the cyanobacteria are cultured in the absence of solar energy. In some embodiments, prior to being mixed with the fermentative microorganism cultures, the cyanobacteria are cultured in an aerated vessel. In some embodiments, prior to being mixed with the fermentative microorganism cultures, the cyanobacteria are cultured in a non-aerated vessel or under anaerobic conditions. In some embodiments, prior to being mixed with the fermentative microorganism cultures, the cyanobacteria are cultured in a vessel purged of oxygen. In some embodiments, prior to being mixed with the fermentative microorganism cultures, the cyanobacteria are cultured in a vessel purged of nitrogen. In some embodiments, prior to being mixed with the fermentative microorganism cultures, the cyanobacteria are cultured in a culture medium that comprises a fermentation product at a concentration of at least 0.01%, 0.02%, 0.03%, 0.04%, 0.05%, 0.06%, 0.07%, 0.08%, 0.09% 0.1%, 0.2%, 0.3%, 0.4%, 0.5%, 0.6%, 0.7%, 0.8%, 0.9%, 1.0%, 1.5%, 2.0%, 5.0%, 10%, 20%, 30%, 50%, or 70% (v/v).

In some embodiments, prior to being mixed with the fermentative microorganism cultures, the cyanobacteria are cultured for greater than 1, 5, 10, 15, 20, 25, 30, 40, 45, 50, 55, 60, 70, 75, 80, 90, 100, 150, or 200 days. In some embodiments, prior to being mixed with the fermentative microorganism cultures, the cyanobacteria are cultured until they reach greater than mid-log phase growth.

In some embodiments, prior to being mixed with the cyanobacteria cultures, the fermentative microorganisms are cultured under a light/dark regime with a range of hours of light:hours of dark, such as 8:16, 9:15, 10:14, 11:13, 12:12, 13:11, 14:10, 15:9, or 16:8. In some cases, the light/dark regime may be cycles wherein the cultures are cultured under light conditions for a certain amount of hours, followed by culture under dark conditions for a certain amount of hours. For example, a light/dark cycle could be 10 hours light/14 hours dark. Repeated light/dark cycles may be conducted over a period of time, such as a period of time greater than 1, 5, 10, 15, 20, 25, 30, 40, 45, 50, 55, 60, 70, 75, 80, 90, 100, 150, or 200 days. In some cases, the light phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5 or 24, hours. In some cases, the dark phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours.

In some embodiments, prior to being mixed with the cyanobacteria cultures, the fermentative microorganisms are cultured in the presence of solar energy. In some embodiments, prior to being mixed with the cyanobacteria cultures, the fermentative microorganisms are cultured in the presence of artificial light (e.g., 150 W halogen light). In some embodiments, prior to being mixed with the cyanobacteria cultures, the fermentative microorganisms are cultured in the absence of solar energy. In some embodiments, prior to being mixed with the cyanobacteria cultures, the fermentative microorganisms are cultured in an aerated vessel. In some embodiments, prior to being mixed with the cyanobacteria cultures, the fermentative microorganisms are cultured in a non-aerated vessel or under anaerobic conditions. In some embodiments, prior to being mixed with the cyanobacteria cultures, the fermentative microorganisms are cultured in a vessel purged of oxygen. In some embodiments, prior to being mixed with the cyanobacteria cultures, the fermentative microorganisms are cultured in a vessel purged of nitrogen. In some embodiments, prior to being mixed with the cyanobacteria cultures, the fermentative microorganisms are cultured in a culture medium that comprises a fermentation product at a concentration of at least 0.01%, 0.02%, 0.03%, 0.04%, 0.05%, 0.06%, 0.07%, 0.08%, 0.09% 0.1%, 0.2%, 0.3%, 0.4%, 0.5%, 0.6%, 0.7%, 0.8%, 0.9%, 1.0%, 1.5%, 2.0%, 5.0%, 10%, 20%, 30%, 50%, or 70% (v/v).

In some embodiments, prior to being mixed with the cyanobacteria cultures, the fermentative microorganisms are cultured for greater than 1, 5, 10, 15, 20, 25, 30, 40, 45, 50, 55, 60, 70, 75, 80, 90, 100, 150, or 200 days. In some embodiments, prior to being mixed with the cyanobacteria cultures, the fermentative microorganisms are cultured until they reach greater than mid-log phase growth.

In some exemplary embodiments, the method comprises growing cyanobacteria in vessels comprising filtered sea water, until the cyanobacteria are well-established (e.g., at a cells/ml concentration described herein). In some embodiments, the method further comprises adding fermentative organisms directly to the cyanobacteria culture. In some embodiments, the method further comprises using counter-current membrane filtration, or other means, to separate the resulting solution. In some embodiments, the method further comprises separating the resulting solution in order to recover a fermentation product, as described herein.

In some embodiments, the co-culture is maintained by replacing lost volumes with fresh filtered sea water, either continuously, or at timed intervals. Such continuous culture is known in the art, and described further herein.

Feedstock and Culture Media

The feedstocks for the fermentative microorganisms of the present disclosure are generally derived from any cyanobacteria described herein. In some cases, the feedstock is derived entirely from cyanobacteria. In other cases, the feedstock is supplemented with additional components. In some cases, the feedstock has a salt concentration of greater than 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, or 30%. In some cases the feedstock contains sea water. In some cases, the feedstock contains filtered sea water.

Feedstocks disclosed herein may contain nutrients or catabolites secreted by cyanobacteria, which may include, but are not limited to: sugars, inorganic nitrogen compounds, organic nitrogen compounds, and trace elements, and any combinations thereof. The feedstocks disclosed herein, often may be obtained by culturing cyanobacteria (or other organism or mixture of organisms described herein) in a first medium, followed by separation of the cyanobacteria (or other organism or mixture of organisms described herein) in order to obtain a feedstock enriched by cyanobacterial (or other organism or mixture of organisms described herein) secretion products. Examples of sugars secreted by cyanobacteria include but are not limited to: glucose, fructose, sucrose, maltose, rhamnose, and long chain multi-carbon saccharides (EPS). Examples of inorganic nitrogen compounds include but are not limited to: $NH_4+$, and $NO_3-$. Examples of organic nitrogen compounds include but are not limited to: urea, proteins and nitrogen containing amino acids. Examples of trace elements include but are not limited to: Mg, Mn, Zn, Cu, Mo, B, Cu, Fe, or Co.

In some cases, a feedstock contains products released by cyanobacteria and said products provide at least 1%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 15%, 20%, 25%, 30%, 35%, 40%, 45%, 50%, 55%, 60%, 65%, 70%, 75%, 80%, 85%, 90%, 95%, or 100% of the maximum growth requirements for a particular nutrient (e.g., sugar, nitrogen compound) for a specific fermentative microorganism.

An advantage of the invention disclosed herein is that since monosaccharides provided by the cyanobacteria serve as the source of sugar, it is unnecessary to break down complex carbohydrates (e.g., starch or cellulose) into monosaccharide components, which is a process known as Saccharification. Thus, in many embodiments described herein, the method is performed without the necessity of saccharification. In some embodiments, the method is performed without saccharification. In some embodiments, the fermentation product is produced without the need for saccharification.

The sugars and nitrogen compounds may exist in any ratio within the feedstock. Examples of possible ratios of sugar: nitrogen compounds include: about 100:1, 90:1, 80:1, 85:1, 80:1, 75:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50, 1:75, 1:80, 1:85, 1:90, or 1:100. For purposes of the foregoing ratios, the term "nitrogen compounds" may include any inorganic or organic nitrogen compound, separately or in combination.

The compositions provided herein may include only the microorganisms themselves (e.g., cyanobacteria, yeast, etc.). In some cases, the compositions provided herein include the microorganisms in combination with culture medium and/or feedstock. Therefore, a composition provided herein may include one or more microorganisms described herein, and one or more culture medium, feedstock, ingredient of culture medium, and/or ingredient of feedstock, in any possible combination.

A feedstock provided herein can be derived from medium containing cyanobacteria. The feedstock medium may also be derived from medium containing other microorganisms in addition to the cyanobacteria. Or, in some embodiments, the feedstock medium is not derived from cyanobacteria.

In some embodiments, cyanobacteria are removed, or were previously removed, from the feedstock media described herein. Methods of depleting cyanobacteria from a culture are known in the art, and may include, but are not limited to: centrifugation, counter-current membrane filtration, filtration, filtration with a pore filter, separation, decanting, a combination of separation and decanting, microfiltration, and any combination of the foregoing. In some embodiments, the cyanobacteria are depleted using a 0.2 micron filter. In some embodiments, the quantity of cyanobacteria present in the feedstock is less than or equal to 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5%, 10%, 15%, 20%, 25%, 30%, 35%, 40%, 45%, 50%, 55%, 60%, 65%, 75%, 80%, 85%, 90%, 95%, or 100% of the quantity of cyanobacteria present in the medium prior to the depletion process.

In some embodiments, the feedstock medium contains no cyanobacteria. In some embodiments, the feedstock medium is substantially free of cyanobacteria. In some embodiments, the feedstock medium contains cyanobacteria, either live or dead. In some embodiments, the feedstock medium contains a concentration of cyanobacteria less than or equal to 1, 2, 5, 10, $10^2$, $10^3$, $10^4$, $10^5$, $10^6$, $10^7$, $10^8$, $10^9$, $10^{10}$, $10^{11}$, $10^{12}$, $10^{13}$, or $10^{14}$ cells/ml.

In some embodiments, before being depleted from the feedstock medium, the cyanobacteria are cultured under a light/dark regime. In some cases, the light/dark regime may be cycles wherein the cultures are cultured under light conditions for a certain amount of hours, followed by culture under dark conditions for a certain amount of hours. For example, a light/dark cycle could be a range of hours of light:hours of dark, such as 8:16, 9:15, 10:14, 11:13, 12:12, 13:11, 14:10, 15:9, or 16:8. Repeated light/dark cycles may be conducted over a period of time, such as a period of time greater than 1, 5, 10, 15, 20, 25, 30, 40, 45, 50, 55, 60, 70, 75, 80, 90, 100, 150, or 200 days. In some cases, the light phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours. In some cases, the dark phase of a light/dark cycle is greater than or equal to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours.

In some embodiments, before being depleted from the feedstock medium, the cyanobacteria are cultured in the presence of solar energy. In some embodiments, before being depleted from the feedstock medium, the cyanobacteria are cultured in the presence of artificial light (e.g., 150 W halogen light). In some embodiments, before being depleted from the feedstock medium, the cyanobacteria are cultured in the absence of solar energy. In some embodiments, before being depleted from the feedstock medium, the cyanobacteria are cultured in an aerated vessel. In some embodiments before being depleted from the feedstock medium, the cyanobacteria are cultured in a non-aerated vessel or under anaerobic conditions. In some embodiments, before being depleted from the feedstock medium, the cyanobacteria are cultured in a vessel purged of oxygen. In some embodiments, before being depleted from the feedstock medium, the cyanobacteria are cultured in a vessel purged of nitrogen. In some embodiments, before being depleted from the feedstock medium, the cyanobacteria are cultured in a culture medium that comprises a fermentation product at a concentration of at least 0.01%, 0.02%, 0.03%, 0.04%, 0.05%, 0.06%, 0.07%, 0.08%, 0.09% 0.1%, 0.2%, 0.3%, 0.4%, 0.5%, 0.6%, 0.7%, 0.8%, 0.9%, 1.0%, 1.5%, 2.0%, 5.0%, 10%, 20%, 30%, 50%, or 70% (v/v).

In some embodiments, before being depleted from the feedstock medium, the cyanobacteria are cultured for greater than 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 days. In some embodiments, before being depleted from the feedstock medium, the cyanobacteria are cultured until they reach greater than mid-log phase growth.

In some embodiments, the cyanobacteria are cultured for greater than 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 days prior to either being combined with fermentative microorganisms, or prior to removal of the cyanobacteria to produce a feedstock described herein.

In some exemplary embodiments, a method of producing feedstock comprises obtaining, purchasing or collecting sea water. The sea water is then filtered with an 0.2 micron filter to remove all organisms. In some embodiments, the method further comprises growing stock cultures of cyanobacteria (e.g., *Synechococcus* CCMP 2669) on defined media or on filtered sea water, or unfiltered sea water. In some embodiments, the method further comprises inoculating vessels containing defined medium or filtered sea water with stock cultures of fermentative microorganisms. In some embodiments, the method further comprises optimizing the conditions for optimal growth under natural air and sunlight conditions. The method may also comprise determining any nutrient deficiencies or limiting factors. In some embodiments, the method further comprises removing cyanobacteria from the vessel using a method described herein (e.g., filtration, centrifugation, etc.) in order to obtain a feedstock. In some embodiments, the method further comprises culturing selected fermentative microorganisms in said feedstock. In some embodiments, the method further comprises removing the fermentative microorganisms (and any other microorganisms) from said culture of fermentative organisms in said feedstock through any method described herein (e.g., centrifugation, filtration, etc.). The method may further comprise processing the solution further to recover a product of interest (e.g., a fermentation product).

Recovery of Fermentation Products, and Additional Culturing Techniques and Equipment Methods are provided for the recovery of fermentation products, such as an alcohol (e.g. ethanol, propanol, methanol, butanol, isobutanol, etc.) another biofuel, biopolymer, biopolymer precursor, bioisoprene, or chemical product. In some cases, broth from the microorganisms is harvested at some point during the fermentation, and fermentation products are recovered. The broth with the fermentation product (e.g., ethanol) to be recovered may include both a fermentation product (e.g., ethanol) and impurities. The impurities include materials such as water, cell bodies, cellular debris, excess carbon substrate, excess nitrogen substrate, other remaining nutrients, non-ethanol metabolites, and other medium components or digested medium components. During the course of processing the broth, the broth can be heated and/or reacted with various reagents, resulting in additional impurities in the broth.

In some embodiments, the processing steps to recover a fermentation product (e.g., ethanol) frequently includes several separation steps, including, for example, distillation of a fermentation product (e.g., ethanol) material from an impure material or liquid, containing a fermentation product (e.g., ethanol). In some embodiments, the result is a yield material or liquid with a high concentration a fermentation product (e.g., ethanol). The high concentration fermentation product (e.g., ethanol) material can be further purified and concentrated to achieve very high concentration fermentation product (e.g., ethanol), such as 98% or 99% or 99.5% (wt.) or even higher (e.g., absolute ethanol). Other separation steps, such as filtration, centrifugation, extraction, adsorption, etc. can also be a part of some recovery processes for a fermentation product (e.g., ethanol) as a product or biofuel, or other biofuels, biopolymers, biopolymer precursors, or chemical products.

In some embodiments, a fermentation product recovery process can be scaled to produce commercially useful biofuels. In further embodiments, scaling a process for fermentation product recovery involves development of facilities and/or industrial sites that use cyanobacteria as the primary sugar feedstock source to produce fuel (e.g., various alcohols such as ethanol, propanol, methanol, butanol, isobutanol, etc.). In still further embodiments, fuel produced at such facilities and/or industrial sites is suited for, lighting, cooking, and transportation uses. In some embodiments, commercial facilities and/or industrial sites employing a scaled process produce electrical energy from co-generation of facility generated biomass. In some embodiments, commercial facilities and/or industrial sites employing a scaled process produce bioproducts (e.g., polymers, personal care products, pharmaceuticals, flavorings, etc.) from fermentation of sugars by appropriate organisms. In other embodiments, commercial facilities and/or industrial sites employing a scaled process use biomass for agricultural or aquaculture purposes. In some embodiments, commercial facilities and/or industrial sites employing a scaled process derive other useful commodities (e.g., salt, nutritional supplements, etc.) from by-products of the process.

The methods described herein can include business methods. The methods described herein, for example, enable highly efficient and cost-effective production of fuels, bioproducts, commodities, sugars, etc. Often, the methods described herein may be performed with limited depletion of resources. The business methods may comprise: producing a feedstock by a method described herein; purifying said feedstock; and packaging said feedstock for use in the production of biofuels or other products. In some embodiments, the business method further comprises selling said feedstock. In some cases, the business methods comprises: producing a feedstock by a method described herein; selling said feedstock; and selling commodities derived from by-products of said producing a feedstock.

Figure 6:
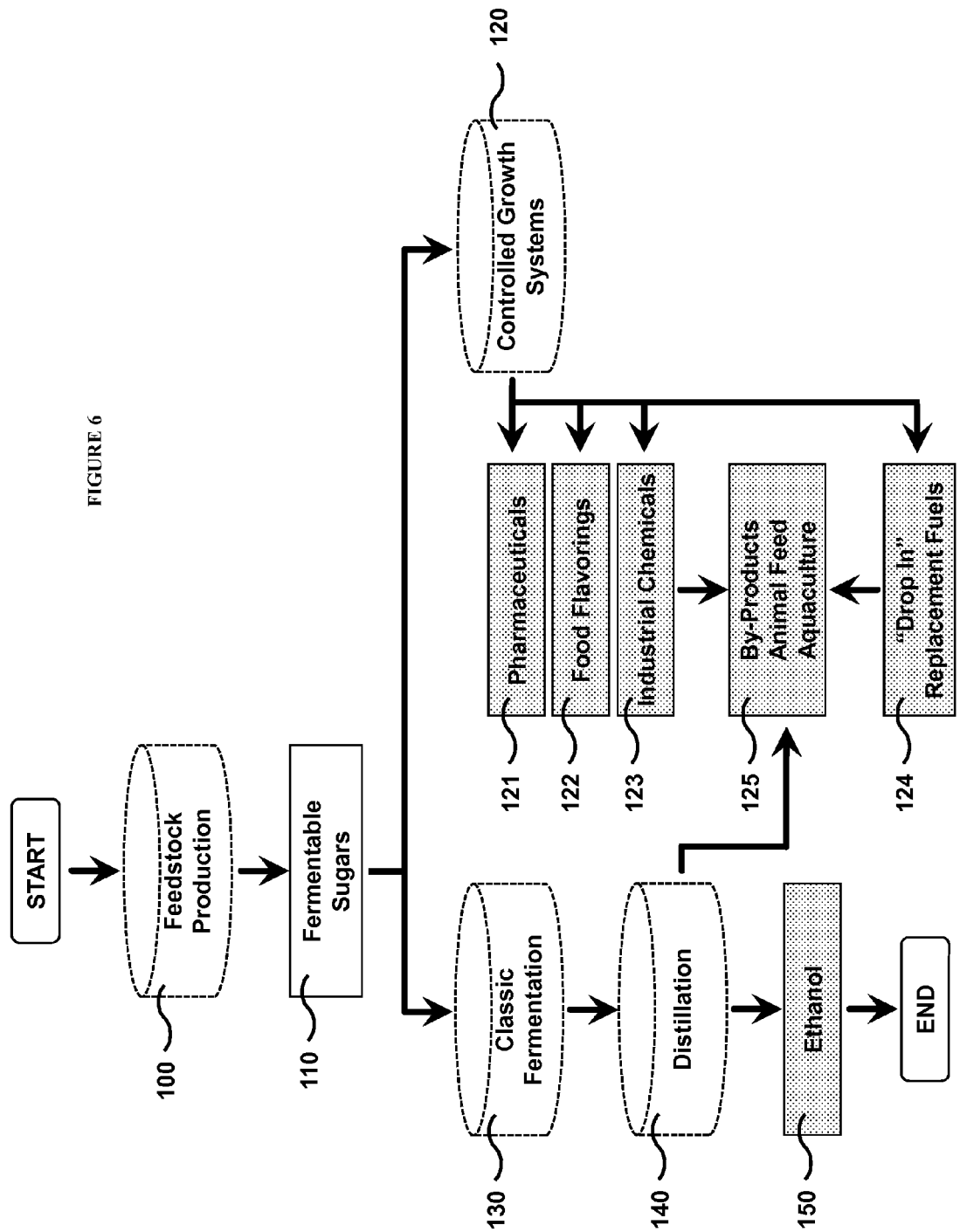
FIG. 6 is a non-limiting, exemplary process flow, wherein feedstock including fermentable sugars is introduced to a fermentation process.

Referring to FIG. 6, in a particular non-limiting embodiment, an overall process includes feedstock production 100 by cyanobacteria cultured in seawater, wherein the cyanobacteria produce fermentable sugars 110 (e.g., sucrose, glucose, fructose, and maltose). In some embodiments, feedstock including fermentable sugars 110 is introduced to classic fermentation 130 followed by distillation 140 with the goal of producing an alcohol such as ethanol 150. In some embodiments, feedstock including fermentable sugars 110 is introduced to one or more controlled growth systems 120 with the goal of producing other commercially useful bioproducts such as pharmaceuticals 121, food flavorants 122, industrial chemicals 123, and drop-in replacement fuels 124. In further embodiments, by-products of the distillation process and/or the processes involved in producing other bioproducts are used to produce feeds used in agriculture or aquaculture 125.

Figure 7:
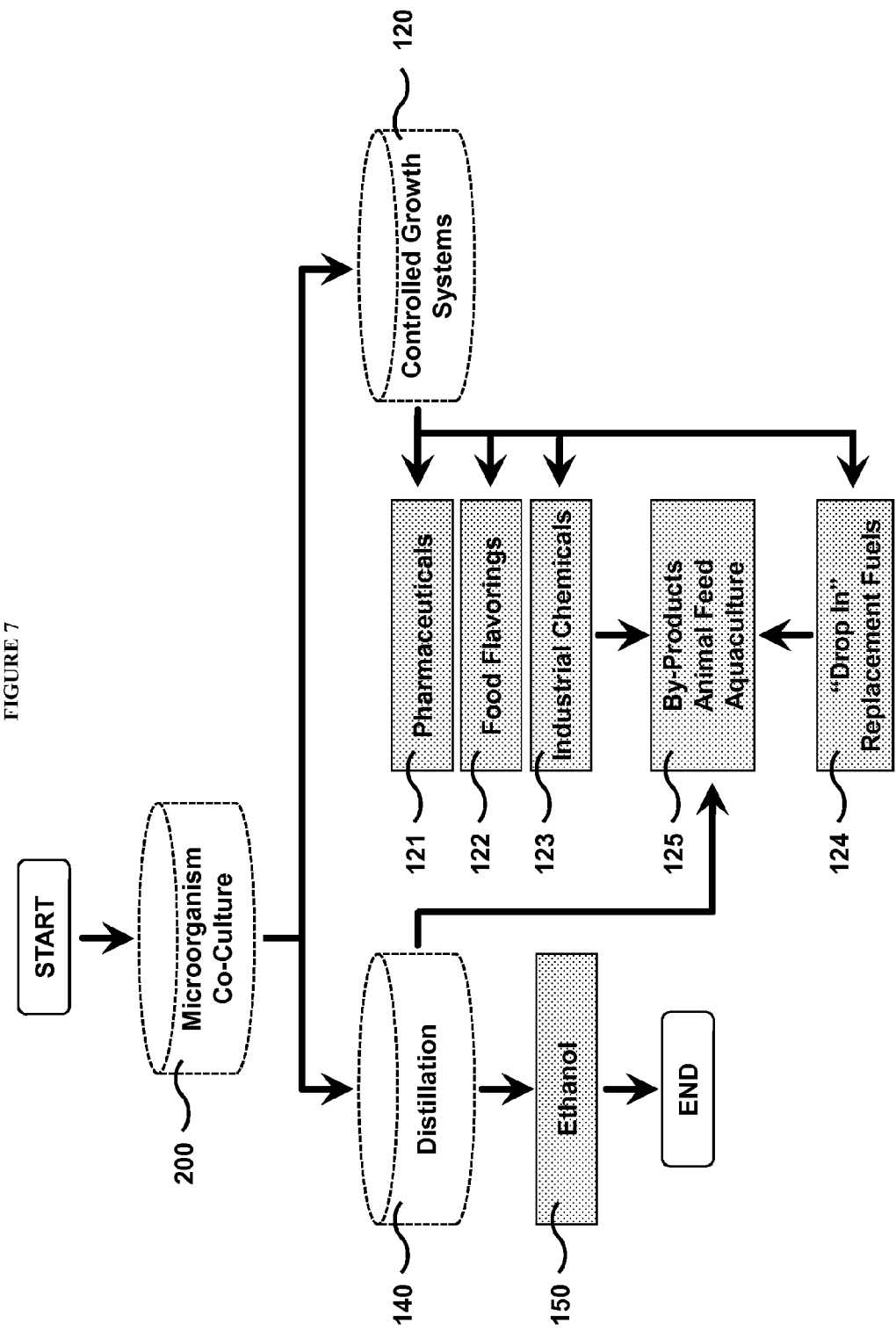
FIG. 7 is a non-limiting, exemplary process flow, wherein microorganisms producing feedstock including fermentable sugars are co-cultured with fermentative microorganisms.

Referring to FIG. 7, in another particular non-limiting embodiment, an overall process includes a co-culture 200 of cyanobacteria, which produce fermentable sugars, and fermentative microorganisms (e.g., yeast), which convert the sugars to bioproducts such as alcohols. In some embodiments, the co-culture, containing fermentation products (e.g., bioproducts), is subjected to distillation 140 with the goal of producing an alcohol such as ethanol 150. In some embodiments, the co-culture is introduced to one or more controlled growth systems 120 with the goal of producing other commercially useful bioproducts such as pharmaceuticals 121, food flavorants 122, industrial chemicals 123, and drop-in replacement fuels 124. In further embodiments, by-products of the distillation process and/or the processes involved in producing other bioproducts are used to produce feeds used in agriculture or aquaculture 125.

In some embodiments, the feeding strategy balances the cell production rate and the rate of hydrolysis of the biomass feedstock with the production of ethanol. Sufficient medium components are added in quantities to achieve sustained cell production and hydrolysis of the biomass feedstock with production of ethanol. In some embodiments, sufficient carbon and nitrogen substrate are added in quantities to achieve sustained production of fresh cells and hydrolytic enzymes for conversion of polysaccharides into lower sugars as well as sustained conversion of the lower sugars into fresh cells and ethanol.

In some cases, the level of a medium component is maintained at a desired level by adding additional medium component as the component is consumed or taken up by the organism. Examples of medium components included, but are not limited to, water, carbon substrate, nitrogen substrate, vitamins, minerals, growth factors, cofactors, and biocatalysts. The medium component can be added continuously or at regular or irregular intervals.

In some embodiments, a continuous feed and/or harvest system known in the art may be used. Such system may be suited for commercial applications and large-scale production of a fermentation product. However, for particular large-scale uses, a system that takes advantage of open ponds adjacent to coastal areas may be employed.

Often, the microorganisms are grown, singly or in co-culture, in a flow-through, steady state system. In some embodiments, the cyanobacteria are grown in a tank, and the tank is separate from the tank housing the fermentative microorganisms (e.g., yeast, fermentative bacteria, etc.). The medium may be pumped by membrane "by-pass" filters to separate spent medium (feedstock) from the cyanobacteria, and permitting the flow through of the spent medium. The spent medium is then pumped into the tanks housing fermentative microorganisms. After fermentation occurs and a fermentative product is produced, membrane filtration, followed by distillation, is used to collect the fermentation products.

The culturing system used for the present invention may be of various designs, components, and sizes. In some embodiments, the system includes one or more of the following elements: a water supply, membrane "by-pass" filtration, culture tanks, pumps, and plumbing. In some embodiments, the system further comprises a back-up power supply and/or means to remove settleable solids.

Methods of continuously culturing and batch culturing microorganisms are known in the art, see, e.g., U.S. Pat. No. 6,596,521, U.S. Pat. No. 4,764,471, International Application Publication No. WO0102534, and U.S. Pat. No. 7,662,617. In some embodiments, cyanobacteria are placed in a continuous culture system and maintained by replacing lost volumes with sea water or filtered sea water. In some embodiments, fermentative microorganisms are placed in a continuous culture system and maintained by replacing lost volumes with supernatant (or feedstock) derived from cyanobacteria cultures. In some embodiments, supernatant (or feedstock) derived from cyanobacterial cultures may be directed to several different systems or cultures of fermentative microorganisms. In some embodiments, cyanobacteria are placed in one vessel of a culture system and fermentative microorganisms are placed in a second vessel of a culture system. The fermentative microorganisms are then continuously fed with medium filtered from the cyanobacteria vessel. In some embodiments, enclosed powered bioreactors are used.

In preferred embodiments, an aquaculture type system is used to culture the microorganisms of the present disclosure. In some embodiments, an open aquaculture type system is used. In some embodiments open aquaculture systems used to cultivate fish are adapted to grow cyanobacteria and/or fermentative microorganisms.

In some embodiments, additional medium components are added prior to the complete depletion of the medium component in the medium. In some embodiments, complete or partial depletion can effectively be used, for example to initiate different metabolic pathways, to simplify downstream operations, or for other reasons as well.

In some embodiments, the nitrogen level is maintained at a desired level by adding additional nitrogen-containing material as nitrogen is consumed or taken up by the organism. The nitrogen-containing material can be added continuously or at regular or irregular intervals. In some embodiments, additional nitrogen-containing material is added prior to the complete or partial depletion of the nitrogen available in the medium. In some embodiments, complete depletion can effectively be used, for example to initiate different metabolic pathways and/or to simplify downstream processing. Useful nitrogen levels include levels of about 5 to about 10 g/L. In one embodiment levels of about 1 to about 12 g/L can also be usefully employed. In another embodiment levels, such as about 0.5, 0.1 g/L or even lower, and higher levels, such as about 20, 30 g/L or even higher are used. In another embodiment a useful nitrogen level is about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22 23, 24, 25, 26, 27, 28, 29 or 30 g/L. Such nitrogen levels can facilitate the production of fresh cells and of hydrolytic enzymes. Increasing the level of nitrogen can lead to higher levels of enzymes and/or greater production of cells, and result in higher productivity of desired products. Nitrogen can be supplied as a simple nitrogen-containing material, such as an ammonium compounds (e.g. ammonium sulfate, ammonium hydroxide, ammonia, ammonium nitrate, or any other compound or mixture containing an ammonium moiety), nitrate or nitrite compounds (e.g. potassium, sodium, ammonium, calcium, or other compound or mixture containing a nitrate or nitrite moiety), or as a more complex nitrogen-containing material, such as amino acids, proteins, hydrolyzed protein, hydrolyzed yeast, yeast extract, dried brewer's yeast, yeast hydrolysates, distillers' grains, soy protein, hydrolyzed soy protein, fermentation products, and processed or corn steep powder or unprocessed protein-rich vegetable or animal matter, including those derived from bean, seeds, soy, legumes, nuts, milk, pig, cattle, mammal, fish, as well as other parts of plants and other types of animals. Nitrogen-containing materials useful in various embodiments also include materials that contain a nitrogen-containing material, including, but not limited to mixtures of a simple or more complex nitrogen-containing material mixed with a carbon source, another nitrogen-containing material, or other nutrients or non-nutrients.

In some cases, the carbon level is maintained at a desired level by adding sugar compounds or material containing sugar compounds as sugar is consumed or taken up by the organism. The sugar-containing material can be added continuously or at regular or irregular intervals. In some embodiments, additional sugar-containing material is added prior to the complete or partial depletion of the sugar compounds available in the medium. In some embodiments, the carbon level can be maintained at a level of about 5 to about 120 g/L. However, levels of about 30 to about 100 g/L can also be usefully employed as well as levels of about 60 to about 80 g/L. In some embodiments, the carbon level is maintained at greater than 25 g/L for a portion of the culturing. In some embodiments, the carbon level is maintained at about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 101 g/L, 102 g/L, 103 g/L, 104 g/L, 105 g/L, 106 g/L, 107 g/L, 108 g/L, 109 g/L, 110 g/L, 111 g/L, 112 g/L, 113 g/L, 114 g/L, 115 g/L, 116 g/L, 117 g/L, 118 g/L, 119 g/L, 120 g/L, 121 g/L, 122 g/L, 123 g/L, 124 g/L, 125 g/L, 126 g/L, 127 g/L, 128 g/L, 129 g/L, 130 g/L, 131 g/L, 132 g/L, 133 g/L, 134 g/L, 135 g/L, 136 g/L, 137 g/L, 138 g/L, 139 g/L, 140 g/L, 141 g/L, 142 g/L, 143 g/L, 144 g/L, 145 g/L, 146 g/L, 147 g/L, 148 g/L, 149 g/L, or 150 g/L.

The carbon substrate, like the nitrogen substrate, is necessary for cell production and enzyme production, but unlike the nitrogen substrate, it serves as the raw material for ethanol. Frequently, more carbon substrate can lead to greater production of ethanol. In another embodiment, it can be advantageous to operate with the carbon level and nitrogen level related to each other for at least a portion of the fermentation time. In some embodiments, the ratio of carbon to nitrogen is maintained within a range of about 30:1 to about 10:1. In some embodiments, the ratio of carbon nitrogen is maintained from about 20:1 to about 10:1 or more preferably from about 15:1 to about 10:1. In some embodiments, the ratio of carbon nitrogen is about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

Maintaining the ratio of carbon to nitrogen within particular ranges can result in benefits to the operation such as the rate of hydrolysis of carbon substrate, which depends on the amount of carbon substrate and the amount and activity of enzymes present, being balanced to the rate of ethanol production. Such balancing can be important, for example, due to the possibility of inhibition of cellular activity due to the presence of a high concentration of low molecular weight saccharides, and the need to maintain enzymatic hydrolytic activity throughout the period where longer chain saccharides are present and available for hydrolysis. Balancing the carbon to nitrogen ratio can, for example, facilitate the sustained production of these enzymes such as to replace those which have lost activity.

In another embodiment, the amount and/or timing of carbon, nitrogen, or other medium component addition can be related to measurements taken during the fermentation. For example, the amount of monosaccharides present, the amount of insoluble polysaccharide present, the polysaccharase activity, the amount of ethanol present, the amount of cellular material (for example, packed cell volume, dry cell weight, etc.) and/or the amount of nitrogen (for example, nitrate, nitrite, ammonia, urea, proteins, amino acids, etc.) present can be measured. The concentration of the particular species, the total amount of the species present in the fermentor, the number of hours the fermentation has been running, and the volume of the fermentor can be considered. In various embodiments, these measurements can be compared to each other and/or they can be compared to previous measurements of the same parameter previously taken from the same fermentation or another fermentation. Adjustments to the amount of a medium component can be accomplished such as by changing the flow rate of a stream containing that component or by changing the frequency of the additions for that component.

In some embodiments, different levels or complete depletion of a medium component can effectively be used, for example to initiate different metabolic pathways or to change the yield of the different products of the fermentation process. For instance, different levels or complete depletion of a medium component can effectively be used to increase the ethanol yield and productivity, to improve carbon utilization (e.g., g ethanol/g sugar fermented) and reduced acid production (e.g., g acid/g ethanol and g acid/g sugar fermented). In some embodiments, different levels or complete depletion of nitrogen can effectively be used to increase the ethanol yield and productivity, to improve carbon utilization (e.g., g ethanol/g sugar fermented) and reduced acid production (e.g., g acid/g ethanol and g acid/g sugar fermented). In some embodiments, different levels or complete depletion of carbon can effectively be used to increase the ethanol yield and productivity, to improve carbon utilization (e.g., g ethanol/g sugar fermented) and reduced acid production (e.g., g acid/g ethanol and g acid/g sugar fermented). In some embodiments, the ratio of carbon level to nitrogen level for at least a portion of the fermentation time can effectively be used to increase the ethanol yield and productivity, to improve carbon utilization (e.g., g ethanol/g sugar fermented) and reduced acid production (e.g., g acid/g ethanol and g acid/g sugar fermented).

In another embodiment, a fed batch operation can be employed, wherein medium components and/or fresh cells are added during the fermentation without removal of a portion of the broth for harvest prior to the end of the fermentation. In one embodiment a fed-batch process is based on feeding a growth limiting nutrient medium to a culture of microorganisms. In one embodiment the feed medium is highly concentrated to avoid dilution of the bioreactor. In another embodiment the controlled addition of the nutrient directly affects the growth rate of the culture and avoids overflow metabolism such as the formation of side metabolites. In one embodiment the growth limiting nutrient is a nitrogen source or a saccharide source.

In another embodiment, a modified fed batch operation can be employed wherein a portion of the broth is harvested at discrete times. Such a modified fed batch operation can be advantageously employed when, for example, very long fermentation cycles are employed. Under very long fermentation conditions, the volume of liquid inside the fermentor increases. In order to operate for very long periods, it can be advantageous to partially empty the fermentor, for example, when the volume is nearly full. A partial harvest of broth followed by supplementation with fresh medium ingredients, such as with a fed batch operation, can improve fermentor utilization and can facilitate higher plant throughputs due to a reduction in the time for tasks such as cleaning and sterilization of equipment. When the "partial harvest" type of operation is employed, the fermentation can be seeded with the broth that remains in the fermentor, or with fresh inoculum, or with a mixture of the two. In addition, broth can be recycled for use as fresh inoculum either alone or in combination with other fresh inoculum.

In some embodiments, the cultures of the present disclosure are started with an inoculum of microorganisms that is more than 10%, 15%, 20%, 25%, 30%, 35%, or 40% of the total culture.

In some embodiments, a fed-batch fermentation for production of fermentation products is used. In another embodiment, a fed-batch fermentation for production of ethanol is used. Fed-batch culture is a kind of microbial process in which medium components, such as carbon substrate, nitrogen substrate, vitamins, minerals, growth factors, cofactors, etc. or biocatalysts (including, for example, fresh organisms) are supplied to the fermentor during cultivation, but culture broth is not harvested at the same time and volume. To improve bioconversion from soluble and insoluble substrates, such as those that can be used in biofuels production, various feeding strategies can be used to improve yields and/or productivity. This technique can be used to achieve a high cell density within a given time. It can also be used to maintain a good supply of nutrients and substrates for the bioconversion process. It can also be used to achieve higher titer and productivity of desirable products that might otherwise be achieved more slowly or not at all.

In some embodiments, a fed batch operation can be employed, wherein medium components and/or fresh cells are added during the fermentation when the hydrolytic activity of the broth has decreased. In some embodiments, medium components and/or fresh cells are added during the fermentation when the hydrolytic activity of the broth has decreased about 5%, 10%, 15%, 20%, 25%, 30%, 35%, 40%, 45%, 50%, 55%, 60%, 65%, 75%, 80%, 85%, 90%, 95%, or 100%.

In various embodiments, particular medium components can have beneficial effects on the performance of the fermentation, such as increasing the titer of desired products, or increasing the rate that the desired products are produced. Specific compounds can be supplied as a specific, pure ingredient, such as a particular amino acid, or it can be supplied as a component of a more complex ingredient, such as using a microbial, plant or animal product as a medium ingredient to provide a particular amino acid, promoter, cofactor, or other beneficial compound.

In some embodiments, beneficial fermentation results can be achieved by adding yeast extract. The addition of the yeast extract can result in increased ethanol titer in batch fermentation, improved productivity and reduced production of side products such as organic acids. In some embodiments, beneficial results with yeast extract can be achieved at usage levels of about 0.5 to about 50 g/L, about 5 to about 30 g/L, or about 10 to about 30 g/L. In another embodiment the yeast extract is used at level about 0.5 g/L, 0.6 g/L, 0.7 g/L, 0.8 g/L, 0.9 g/L, 1 g/L, 1.1 g/L, 1.2 g/L, 1.3 g/L, 1.4 g/L, 1.5 g/L, 1.6 g/L, 1.7 g/L, 1.8 g/L, 1.9 g/L, 2 g/L, 2.1 g/L, 2.2 g/L, 2.3 g/L, 2.4 g/L, 2.5 g/L, 2.6 g/L, 2.7 g/L, 2.8 g/L, 2.9 g/L, 3 g/L, 3.1 g/L, 3.2 g/L, 3.3 g/L, 3.4 g/L, 3.5 g/L, 3.6 g/L, 3.7 g/L, 3.8 g/L, 3.9 g/L, 4 g/L, 4.1 g/L, 4.2 g/L, 4.3 g/L, 4.4 g/L, 4.5 g/L, 4.6 g/L, 4.7 g/L, 4.8 g/L, 4.9 g/L, 5 g/L, 5.1 g/L, 5.2 g/L, 5.3 g/L, 5.4 g/L, 5.5 g/L, 5.6 g/L, 5.7 g/L, 5.8 g/L, 5.9 g/L, 6 g/L, 6.1 g/L, 6.2 g/L, 6.3 g/L, 6.4 g/L, 6.5 g/L, 6.6 g/L, 6.7 g/L, 6.8 g/L, 6.9 g/L, 7 g/L, 7.1 g/L, 7.2 g/L, 7.3 g/L, 7.4 g/L, 7.5 g/L, 7.6 g/L, 7.7 g/L, 7.8 g/L, 7.9 g/L, 8 g/L, 8.1 g/L, 8.2 g/L, 8.3 g/L, 8.4 g/L, 8.5 g/L, 8.6 g/L, 8.7 g/L, 8.8 g/L, 8.9 g/L, 9 g/L, 9.1 g/L, 9.2 g/L, 9.3 g/L, 9.4 g/L, 9.5 g/L, 9.6 g/L, 9.7 g/L, 9.8 g/L, 9.9 g/L, 10 g/L, 10.1 g/L, 10.2 g/L, 10.3 g/L, 10.4 g/L, 10.5 g/L, 10.6 g/L, 10.7 g/L, 10.8 g/L, 10.9 g/L, 11 g/L, 11.1 g/L, 11.2 g/L, 11.3 g/L, 11.4 g/L, 11.5 g/L, 11.6 g/L, 11.7 g/L, 11.8 g/L, 11.9 g/L, 12 g/L, 12.1 g/L, 12.2 g/L, 12.3 g/L, 12.4 g/L, 12.5 g/L, 12.6 g/L, 12.7 g/L, 12.8 g/L, 12.9 g/L, 13 g/L, 13.1 g/L, 13.2 g/L, 13.3 g/L, 13.4 g/L, 13.5 g/L, 13.6 g/L, 13.7 g/L, 13.8 g/L, 13.9 g/L, 14 g/L, 14.1 g/L, 14.2 g/L, 14.3 g/L, 14.4 g/L, 14.5 g/L, 14.6 g/L, 14.7 g/L, 14.8 g/L, 14.9 g/L, 15 g/L, 15.1 g/L, 15.2 g/L, 15.3 g/L, 15.4 g/L, 15.5 g/L, 15.6 g/L, 15.7 g/L, 15.8 g/L, 15.9 g/L, 16 g/L, 16.1 g/L, 16.2 g/L, 16.3 g/L, 16.4 g/L, 16.5 g/L, 16.6 g/L, 16.7 g/L, 16.8 g/L, 16.9 g/L, 17 g/L, 17.1 g/L, 17.2 g/L, 17.3 g/L, 17.4 g/L, 17.5 g/L, 17.6 g/L, 17.7 g/L, 17.8 g/L, 17.9 g/L, 18 g/L, 18.1 g/L, 18.2 g/L, 18.3 g/L, 18.4 g/L, 18.5 g/L, 18.6 g/L, 18.7 g/L, 18.8 g/L, 18.9 g/L, 19 g/L, 19.1 g/L, 19.2 g/L, 19.3 g/L, 19.4 g/L, 19.5 g/L, 19.6 g/L, 19.7 g/L, 19.8 g/L, 19.9 g/L, 20 g/L, 20.1 g/L, 20.2 g/L, 20.3 g/L, 20.4 g/L, 20.5 g/L, 20.6 g/L, 20.7 g/L, 20.8 g/L, 20.9 g/L, 21 g/L, 21.1 g/L, 21.2 g/L, 21.3 g/L, 21.4 g/L, 21.5 g/L, 21.6 g/L, 21.7 g/L, 21.8 g/L, 21.9 g/L, 22 g/L, 22.1 g/L, 22.2 g/L, 22.3 g/L, 22.4 g/L, 22.5 g/L, 22.6 g/L, 22.7 g/L, 22.8 g/L, 22.9 g/L, 23 g/L, 23.1 g/L, 23.2 g/L, 23.3 g/L, 23.4 g/L, 23.5 g/L, 23.6 g/L, 23.7 g/L, 23.8 g/L, 23.9 g/L, 24 g/L, 24.1 g/L, 24.2 g/L, 24.3 g/L, 24.4 g/L, 24.5 g/L, 24.6 g/L, 24.7 g/L, 24.8 g/L, 24.9 g/L, 25 g/L, 25.1 g/L, 25.2 g/L, 25.3 g/L, 25.4 g/L, 25.5 g/L, 25.6 g/L, 25.7 g/L, 25.8 g/L, 25.9 g/L, 26 g/L, 26.1 g/L, 26.2 g/L, 26.3 g/L, 26.4 g/L, 26.5 g/L, 26.6 g/L, 26.7 g/L, 26.8 g/L, 26.9 g/L, 27 g/L, 27.1 g/L, 27.2 g/L, 27.3 g/L, 27.4 g/L, 27.5 g/L, 27.6 g/L, 27.7 g/L, 27.8 g/L, 27.9 g/L, 28 g/L, 28.1 g/L, 28.2 g/L, 28.3 g/L, 28.4 g/L, 28.5 g/L, 28.6 g/L, 28.7 g/L, 28.8 g/L, 28.9 g/L, 29 g/L, 29.1 g/L, 29.2 g/L, 29.3 g/L, 29.4 g/L, 29.5 g/L, 29.6 g/L, 29.7 g/L, 29.8 g/L, 29.9 g/L, 30 g/L, 30.1 g/L, 30.2 g/L, 30.3 g/L, 30.4 g/L, 30.5 g/L, 30.6 g/L, 30.7 g/L, 30.8 g/L, 30.9 g/L, 31 g/L, 31.1 g/L, 31.2 g/L, 31.3 g/L, 31.4 g/L, 31.5 g/L, 31.6 g/L, 31.7 g/L, 31.8 g/L, 31.9 g/L, 32 g/L, 32.1 g/L, 32.2 g/L, 32.3 g/L, 32.4 g/L, 32.5 g/L, 32.6 g/L, 32.7 g/L, 32.8 g/L, 32.9 g/L, 33 g/L, 33.1 g/L, 33.2 g/L, 33.3 g/L, 33.4 g/L, 33.5 g/L, 33.6 g/L, 33.7 g/L, 33.8 g/L, 33.9 g/L, 34 g/L, 34.1 g/L, 34.2 g/L, 34.3 g/L, 34.4 g/L, 34.5 g/L, 34.6 g/L, 34.7 g/L, 34.8 g/L, 34.9 g/L, 35 g/L, 35.1 g/L, 35.2 g/L, 35.3 g/L, 35.4 g/L, 35.5 g/L, 35.6 g/L, 35.7 g/L, 35.8 g/L, 35.9 g/L, 36 g/L, 36.1 g/L, 36.2 g/L, 36.3 g/L, 36.4 g/L, 36.5 g/L, 36.6 g/L, 36.7 g/L, 36.8 g/L, 36.9 g/L, 37 g/L, 37.1 g/L, 37.2 g/L, 37.3 g/L, 37.4 g/L, 37.5 g/L, 37.6 g/L, 37.7 g/L, 37.8 g/L, 37.9 g/L, 38 g/L, 38.1 g/L, 38.2 g/L, 38.3 g/L, 38.4 g/L, 38.5 g/L, 38.6 g/L, 38.7 g/L, 38.8 g/L, 38.9 g/L, 39 g/L, 39.1 g/L, 39.2 g/L, 39.3 g/L, 39.4 g/L, 39.5 g/L, 39.6 g/L, 39.7 g/L, 39.8 g/L, 39.9 g/L, 40 g/L, 40.1 g/L, 40.2 g/L, 40.3 g/L, 40.4 g/L, 40.5 g/L, 40.6 g/L, 40.7 g/L, 40.8 g/L, 40.9 g/L, 41 g/L, 41.1 g/L, 41.2 g/L, 41.3 g/L, 41.4 g/L, 41.5 g/L, 41.6 g/L, 41.7 g/L, 41.8 g/L, 41.9 g/L, 42 g/L, 42.1 g/L, 42.2 g/L, 42.3 g/L, 42.4 g/L, 42.5 g/L, 42.6 g/L, 42.7 g/L, 42.8 g/L, 42.9 g/L, 43 g/L, 43.1 g/L, 43.2 g/L, 43.3 g/L, 43.4 g/L, 43.5 g/L, 43.6 g/L, 43.7 g/L, 43.8 g/L, 43.9 g/L, 44 g/L, 44.1 g/L, 44.2 g/L, 44.3 g/L, 44.4 g/L, 44.5 g/L, 44.6 g/L, 44.7 g/L, 44.8 g/L, 44.9 g/L, 45 g/L, 45.1 g/L, 45.2 g/L, 45.3 g/L, 45.4 g/L, 45.5 g/L, 45.6 g/L, 45.7 g/L, 45.8 g/L, 45.9 g/L, 46 g/L, 46.1 g/L, 46.2 g/L, 46.3 g/L, 46.4 g/L, 46.5 g/L, 46.6 g/L, 46.7 g/L, 46.8 g/L, 46.9 g/L, 47 g/L, 47.1 g/L, 47.2 g/L, 47.3 g/L, 47.4 g/L, 47.5 g/L, 47.6 g/L, 47.7 g/L, 47.8 g/L, 47.9 g/L, 48 g/L, 48.1 g/L, 48.2 g/L, 48.3 g/L, 48.4 g/L, 48.5 g/L, 48.6 g/L, 48.7 g/L, 48.8 g/L, 48.9 g/L, 49 g/L, 49.1 g/L, 49.2 g/L, 49.3 g/L, 49.4 g/L, 49.5 g/L, 49.6 g/L, 49.7 g/L, 49.8 g/L, 49.9 g/L or 50 g/L.

The yeast extract can also be fed throughout the course of the entire fermentation or a portion of the fermentation, continuously or delivered at intervals. In some embodiments, usage levels include maintaining a nitrogen concentration of about 0.05 g/L to about 3 g/L (as nitrogen). In another embodiment the nitrogen concentration is about 0.05 g/L, 0.06 g/L, 0.07 g/L, 0.08 g/L, 0.09 g/L, 0.1 g/L, 0.11 g/L, 0.12 g/L, 0.13 g/L, 0.14 g/L, 0.15 g/L, 0.16 g/L, 0.17 g/L, 0.18 g/L, 0.19 g/L, 0.2 g/L, 0.21 g/L, 0.22 g/L, 0.23 g/L, 0.24 g/L, 0.25 g/L, 0.26 g/L, 0.27 g/L, 0.28 g/L, 0.29 g/L, 0.3 g/L, 0.31 g/L, 0.32 g/L, 0.33 g/L, 0.34 g/L, 0.35 g/L, 0.36 g/L, 0.37 g/L, 0.38 g/L, 0.39 g/L, 0.4 g/L, 0.41 g/L, 0.42 g/L, 0.43 g/L, 0.44 g/L, 0.45 g/L, 0.46 g/L, 0.47 g/L, 0.48 g/L, 0.49 g/L, 0.5 g/L, 0.51 g/L, 0.52 g/L, 0.53 g/L, 0.54 g/L, 0.55 g/L, 0.56 g/L, 0.57 g/L, 0.58 g/L, 0.59 g/L, 0.6 g/L, 0.61 g/L, 0.62 g/L, 0.63 g/L, 0.64 g/L, 0.65 g/L, 0.66 g/L, 0.67 g/L, 0.68 g/L, 0.69 g/L, 0.7 g/L, 0.71 g/L, 0.72 g/L, 0.73 g/L, 0.74 g/L, 0.75 g/L, 0.76 g/L, 0.77 g/L, 0.78 g/L, 0.79 g/L, 0.8 g/L, 0.81 g/L, 0.82 g/L, 0.83 g/L, 0.84 g/L, 0.85 g/L, 0.86 g/L, 0.87 g/L, 0.88 g/L, 0.89 g/L, 0.9 g/L, 0.91 g/L, 0.92 g/L, 0.93 g/L, 0.94 g/L, 0.95 g/L, 0.96 g/L, 0.97 g/L, 0.98 g/L, 0.99 g/L, 1 g/L, 1.01 g/L, 1.02 g/L, 1.03 g/L, 1.04 g/L, 1.05 g/L, 1.06 g/L, 1.07 g/L, 1.08 g/L, 1.09 g/L, 1.1 g/L, 1.11 g/L, 1.12 g/L, 1.13 g/L, 1.14 g/L, 1.15 g/L, 1.16 g/L, 1.17 g/L, 1.18 g/L, 1.19 g/L, 1.2 g/L, 1.21 g/L, 1.22 g/L, 1.23 g/L, 1.24 g/L, 1.25 g/L, 1.26 g/L, 1.27 g/L, 1.28 g/L, 1.29 g/L, 1.3 g/L, 1.31 g/L, 1.32 g/L, 1.33 g/L, 1.34 g/L, 1.35 g/L, 1.36 g/L, 1.37 g/L, 1.38 g/L, 1.39 g/L, 1.4 g/L, 1.41 g/L, 1.42 g/L, 1.43 g/L, 1.44 g/L, 1.45 g/L, 1.46 g/L, 1.47 g/L, 1.48 g/L, 1.49 g/L, 1.5 g/L, 1.51 g/L, 1.52 g/L, 1.53 g/L, 1.54 g/L, 1.55 g/L, 1.56 g/L, 1.57 g/L, 1.58 g/L, 1.59 g/L, 1.6 g/L, 1.61 g/L, 1.62 g/L, 1.63 g/L, 1.64 g/L, 1.65 g/L, 1.66 g/L, 1.67 g/L, 1.68 g/L, 1.69 g/L, 1.7 g/L, 1.71 g/L, 1.72 g/L, 1.73 g/L, 1.74 g/L, 1.75 g/L, 1.76 g/L, 1.77 g/L, 1.78 g/L, 1.79 g/L, 1.8 g/L, 1.81 g/L, 1.82 g/L, 1.83 g/L, 1.84 g/L, 1.85 g/L, 1.86 g/L, 1.87 g/L, 1.88 g/L, 1.89 g/L, 1.9 g/L, 1.91 g/L, 1.92 g/L, 1.93 g/L, 1.94 g/L, 1.95 g/L, 1.96 g/L, 1.97 g/L, 1.98 g/L, 1.99 g/L, 2 g/L, 2.01 g/L, 2.02 g/L, 2.03 g/L, 2.04 g/L, 2.05 g/L, 2.06 g/L, 2.07 g/L, 2.08 g/L, 2.09 g/L, 2.1 g/L, 2.11 g/L, 2.12 g/L, 2.13 g/L, 2.14 g/L, 2.15 g/L, 2.16 g/L, 2.17 g/L, 2.18 g/L, 2.19 g/L, 2.2 g/L, 2.21 g/L, 2.22 g/L, 2.23 g/L, 2.24 g/L, 2.25 g/L, 2.26 g/L, 2.27 g/L, 2.28 g/L, 2.29 g/L, 2.3 g/L, 2.31 g/L, 2.32 g/L, 2.33 g/L, 2.34 g/L, 2.35 g/L, 2.36 g/L, 2.37 g/L, 2.38 g/L, 2.39 g/L, 2.4 g/L, 2.41 g/L, 2.42 g/L, 2.43 g/L, 2.44 g/L, 2.45 g/L, 2.46 g/L, 2.47 g/L, 2.48 g/L, 2.49 g/L, 2.5 g/L, 2.51 g/L, 2.52 g/L, 2.53 g/L, 2.54 g/L, 2.55 g/L, 2.56 g/L, 2.57 g/L, 2.58 g/L, 2.59 g/L, 2.6 g/L, 2.61 g/L, 2.62 g/L, 2.63 g/L, 2.64 g/L, 2.65 g/L, 2.66 g/L, 2.67 g/L, 2.68 g/L, 2.69 g/L, 2.7 g/L, 2.71 g/L, 2.72 g/L, 2.73 g/L, 2.74 g/L, 2.75 g/L, 2.76 g/L, 2.77 g/L, 2.78 g/L, 2.79 g/L, 2.8 g/L, 2.81 g/L, 2.82 g/L, 2.83 g/L, 2.84 g/L, 2.85 g/L, 2.86 g/L, 2.87 g/L, 2.88 g/L, 2.89 g/L, 2.9 g/L, 2.91 g/L, 2.92 g/L, 2.93 g/L, 2.94 g/L, 2.95 g/L, 2.96 g/L, 2.97 g/L, 2.98 g/L, 2.99 g/L, or 3 g/L.

Various embodiments offer benefits relating to improving the titer and/or productivity of alcohol production by fermentative organisms described herein, by culturing the organism in a medium comprising one or more compounds comprising particular fatty acid moieties and/or culturing the organism under conditions of controlled pH.

The production of high levels of alcohol may be enhanced by the use of organisms that have the ability to thrive generally in the presence of elevated alcohol levels and/or the ability to continue to produce alcohol without undue inhibition or suppression by the alcohol and/or other components present. Frequently, different metabolic pathways are implicated for each of these. For example, pathways related to cell growth generally include those related to protein production, membrane production as well as the production of all of the cellular subsystems necessary for the cell to survive. Pathways related to alcohol production are frequently more specific, such as those pathways related to the metabolism of sugars leading to production of alcohol and the enzymes that are necessary for the production of alcohol and intermediates. The pathway for one alcohol, e.g., ethanol, can share some similar enzymes, etc., but will also have enzymes and substrates unique to that pathway. While there can be some overlap between these sets of pathways, it is not expected that enhancement of one will automatically result in the enhancement of the other.

In some cases, alcohol intolerance or alcohol-induced toxicity can be related to permeabilization of the cell membrane by elevated levels of alcohol, leading to leakage of intracellular enzymes and nutrients. In some other cases, alcohol tolerance and the ability to produce high alcohol titers is related to the ability of intracellular enzymes to withstand denaturing by the alcohol present, e.g., within the cell, whether due to production by the cell itself or from transport across the cell membrane. In some cases, a more robust membrane will allow a higher alcohol gradient to be present across the membrane, thus allowing the cells to grow and/or continue to produce alcohol at higher external alcohol concentrations.

In some embodiments, a fermentative microorganism described herein is fermented at a pH 5-8.5 In some embodiments, the fermentative organism is fermented at pH of about 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, or 8.5.

Fermentation Products

As used herein, the term "fermentation product" includes, but is not limited to any biofuels, biofuel precursors, polymers, polymer precursors, biopolymers, biopolymer precursors, chemicals, and/or compounds suitable as liquid fuels, gaseous fuels, reagents, chemical feedstocks, chemical additives, processing aids, food additives, animal feeds, aquaculture feeds, and other products. Non-limiting examples of fermentation products include: Acetic acid, Acetate, Acetone, 2,3-Butanediol, Butanol, Butyrate, $CO_2$, Ethanol, Formate, Glycolate, Lactate, Malate, Propionate, Pyruvate, and Succinate. Preferably, the fermentation product is ethanol; in other preferred embodiments, the fermentation product is butanol. In some embodiments, the fermentation products are one or more of the following: ethanol, 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3- pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexen e, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexen e, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexen e, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-3-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal. undecanoate, n-dodecane, 1-dodecene, 1-dodecanol, dodecanal, dodecanoate, n-dodecane, 1-decadecene, 1-dodecanol, ddodecanal, dodecanoate, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyebutane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, fucoidan, iodine, chlorophyll, carotenoid, calcium, magnesium, iron, sodium, potassium, phosphate, lactic acid, acetic acid, formic acid, isoprenoids, bioisoprenes, and polyisoprenes, including rubber. Further, such products can include propylene, polypropylene, ethylene glycol, acrylics, succinic acid, pyruvic acid, adipic acid, enzymes such as cellulases, polysaccharases, lipases, proteases, ligninases, and hemicellulases and may be present as a pure compound, a mixture, or an impure or diluted form.

The "conversion efficiency" for the production of a fermentation product can be expressed as a percentage yield of the product from a starting volume of substrate. For example, an efficiency of 10% (v) means that 1000 ml of feedstock solution yields 100 ml of ethanol. The "conversion efficiency" for the production of a fermentation product can also be expressed as a percentage yield of the product from a starting mass of substrate. For the production of ethanol from glucose, the net reaction is generally accepted as:

$$C_6H_{12}O_6 \rightarrow C_2H_5OH + 2CO_2$$

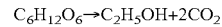

and the theoretical maximum conversion efficiency, or yield, is 51% (wt.). Frequently, the conversion efficiency will be referenced to the theoretical maximum, for example, "80% of the theoretical maximum." In the case of conversion of glucose to ethanol, this statement would indicate a conversion efficiency of 41% (wt.).

The fermentative product yield may often be calculated. The amount of fermentative product (e.g., ethanol) produced may be stated as a mass value per cell (either cyanobacterial cell or fermentative microorganism cell) per day. For example, greater than $1\times10^{-3}$, $1.5\times10^{-3}$, $2\times10^{-3}$, $2.5\times10^{-3}$, $3\times10^{-3}$, $3.5\times10^{-3}$, $4\times10^{-3}$, $4.5\times10^{-3}$, $5\times10^{-3}$, $5.5\times10^{-3}$, $6\times10^{-3}$, $6.5\times10^{-3}$, $7\times10^{-3}$, $7.5\times10^{-3}$, $8\times10^{-3}$, $8.5\times10^{-3}$, $9\times10^{-3}$ or $9.5\times10^{-3}$ mg of fermentative product per cyanobacteria cell may be produced per day. In some cases, greater than $7\times10^{-3}$ mg EtOH is produced per cyanobacteria cell per day. In some embodiments, greater than $1\times10^{-2}$, $1.5\times10^{-2}$, $2\times10^{-2}$, $2.5\times10^{-2}$, $3\times10^{-2}$, $3.5\times10^{-2}$, $4\times10^{-2}$, $4.5\times10^{-2}$, $5\times10^{-2}$, $5.5\times10^{-2}$, $6\times10^{-2}$, $6.5\times10^{-2}$, $7\times10^{-2}$, $7.5\times10^{-2}$, $8\times10^{-2}$, $8.5\times10^{-2}$, $9\times10^{-2}$ or $9.5\times10^{-2}$ mg of fermentative product per cyanobacteria cell may be produced per day. In some embodiments, greater than $1\times10^{-1}$, $1.5\times10^{-1}$, $2\times10^{-1}$, $2.5\times10^{-1}$, $3\times10^{-1}$, $3.5\times10^{-1}$, $4\times10^{-1}$, $4.5\times10^{-1}$, $5\times10^{-1}$, $5.5\times10^{-1}$, $6\times10^{-1}$, $6.5\times10^{-1}$, $7\times10^{-1}$, $7.5\times10^{-1}$, $8\times10^{-1}$, $8.5\times10^{-1}$, $9\times10^{-1}$ or $9.5\times10^{-1}$ mg of fermentative product per cyanobacteria cell may be produced per day. In some cases, greater than $1\times10^{-3}$, $1.5\times10^{-3}$, $2\times10^{-3}$, $2.5\times10^{-3}$, $3\times10^{-3}$, $3.5\times10^{3}$, $4\times10^{3}$, $4.5\times10^{3}$, $5\times10^{3}$, $5.5\times10^{3}$, $6\times10^{3}$, $6.5\times10^{3}$, $7\times10^{3}$, $7.5\times10^{3}$, $8\times10^{3}$, $8.5\times10^{-3}$, $9\times10^{-3}$ or $9.5\times10^{-3}$ mg of fermentative product per fermentative microorganism cell may be produced per day. In some cases, greater than $1\times10^{-2}$, $1.5\times10^{-2}$, $2\times10^{-2}$, $2.5\times10^{-2}$, $3\times10^{-2}$, $3.5\times10^{-2}$, $4\times10^{-2}$, $4.5\times10^{-2}$, $5\times10^{-2}$, $5.5\times10^{-2}$, $6\times10^{-2}$, $6.5\times10^{-2}$, $7\times10^{-2}$, $7.5\times10^{-2}$, $8\times10^{-2}$, $8.5\times10^{-2}$, $9\times10^{-2}$ or $9.5\times10^{-2}$ mg of fermentative product per fermentative microorganism cell may be produced per day. In some embodiments, greater than $1\times10^{-1}$, $1.5\times10^{-1}$, $2\times10^{-1}$, $2.5\times10^{-1}$, $3\times10^{-1}$, $3.5\times10^{-1}$, $4\times10^{-1}$, $4.5\times$ 10⁻¹, 5×10⁻¹, 5.5×10⁻¹, 6×10⁻¹, 6.5×10⁻¹, 7×10⁻¹, 7.5×10⁻¹, 8×10⁻¹, 8.5×10⁻¹, 9×10⁻¹ or 9.5×10⁻¹ mg of fermentative product per fermentative microorganism cell may be produced per day.

In some embodiments, the amount of fermentable product per cyanobacteria cell per day is at least 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 5.0%, 10%, 20%, 30%, 50%, 60%, 70%, 75%, 80%, 90%, 95%, 100%, 150%, 200%, 300%, 400%, 500%, 600%, or 700% of the amount of fermentative product produced per fermentative microorganism (e.g., yeast, etc.) cell per day. In some embodiments, the amount of fermentable product (e.g., sugar) produced per acre per year is greater than 5, 6, 7, 8, 9, 10, 15, 20, 25, 30, 40, 50, 100, 200, 500, 1000, 2000, 3000, or 4000 tons of dry fermentable product per acre per year. For the purposes of comparison, those skilled in the art will recognize that sugar cane typically produces less than 5 tons of dry sugar per acre per year.

Various fermentation conditions can enhance the activities of the organism, resulting in higher yields, higher productivity, greater product selectivity, and/or greater conversion efficiency. In some embodiments, fermentation conditions include fed batch operation and fed batch operation with cell augmentation; addition of complex nitrogen sources such as yeast extract; addition of specific amino acids; addition of a complex material containing one or more amino acids; addition of other nutrients or other compounds. In some embodiments, fermentation conditions can include supplementation of a medium with an organic nitrogen source. In another embodiment, fermentation conditions can include supplementation of a medium with an inorganic nitrogen source.

In some embodiments, a fermentation to produce ethanol is performed by culturing a strain of a fermentative microorganism described herein in a medium described herein. The resulting production of ethanol can be up to 1-fold, 2-fold, 3-fold, 4-fold, 5-fold, 6-fold, 7-fold, 8-fold, 9-fold, and in some cases up to 10-fold and higher in volumetric productivity than a process that does not derive from cyanobacteria, or medium from cyanobacteria, and achieves a carbon conversion efficiency approaching the theoretical maximum. The theoretical maximum can vary with the substrate and product. For example, the maximum conversion efficiency of glucose to ethanol may be 0.51 g ethanol/g glucose. In some embodiments, a fermentative microorganism described herein can produce about 40-100% of a theoretical maximum yield of ethanol. In another embodiment, a fermentative microorganism described herein can produce up to about 40% of the theoretical maximum yield of ethanol. In another embodiment, a fermentative microorganism described herein can produce up to about 50% of the theoretical maximum yield of ethanol. In another embodiment, a fermentative microorganism described herein can produce about 70% of the theoretical maximum yield of ethanol. In another embodiment, a fermentative microorganism described herein can produce about 90% of the theoretical maximum yield of ethanol. In another embodiment, a fermentative microorganism described herein can produce about 95% of the theoretical maximum yield of ethanol. In another embodiment, a fermentative microorganism described herein can produce about 95% of the theoretical maximum yield of ethanol. In another embodiment, a fermentative microorganism described herein can produce about 99% of the theoretical maximum yield of ethanol. In another embodiment, a fermentative microorganism described herein can produce about 100% of the theoretical maximum yield of ethanol. In one embodiment a fermentative microorganism described herein can produce up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of ethanol.

In some embodiments, a fermentative microorganism described herein can produce about 40-100% of a theoretical maximum yield of butanol or other fermentation product described herein. In another embodiment, a fermentative microorganism described herein can produce up to about 40% of the theoretical maximum yield of butanol or other fermentation product described herein. In another embodiment, a fermentative microorganism described herein can produce up to about 50% of the theoretical maximum yield of butanol or other fermentation product described herein. In another embodiment, a fermentative microorganism described herein can produce about 70% of the theoretical maximum yield of butanol or other fermentation product described herein. In another embodiment, a fermentative microorganism described herein can produce about 90% of the theoretical maximum yield of butanol or other fermentation product described herein. In another embodiment, a fermentative microorganism described herein can produce about 95% of the theoretical maximum yield of butanol or other fermentation product described herein. In another embodiment, a fermentative microorganism described herein can produce about 95% of the theoretical maximum yield of butanol or other fermentation product described herein. In another embodiment, a fermentative microorganism described herein can produce about 99% of the theoretical maximum yield of butanol or other fermentation product described herein. In another embodiment, a fermentative microorganism described herein can produce about 100% of the theoretical maximum yield of butanol or other fermentation product described herein. In one embodiment a fermentative microorganism described herein can produce up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of butanol or other fermentation product described herein.

EXAMPLES

Example 1

Z. mobilis Cultured with Centrifuged Feedstock Derived from Synechococcus

Synechococcus CCMP2669 ("Syn") was grown in an automated bioreactor system, using A+medium. The recipe for A+medium is provided in Table 1. The culture was harvested and centrifuged (4000 rpm×g, for 15 minutes). 100 ml of the centrifuged feedstock was transferred to sterile culture vessels and inoculated with 5.0 ml of ethanol producing organisms (either *Saccharomyces cerevisiae* (strain WLP 009) or *Zymononas mobilis*). Cultures were incubated at 35° C. The growth rate of the organisms was monitored using a Klett-Sommerson colorimeter equipped with a blue filter and the ethanol concentration in solution was measured using an enzymatic assay system.

Results show that *Z. mobilis* can grow on feedstock from Syn (FIG. 1). FIG. 1 shows the results from four replicate flasks and demonstrates that the four flasks had near-identical growth rates. A small number of *Synechococcus* cells remained in the feedstock after centrifugation and eventually grew in conjunction with *Z. mobilis*.

Controls containing only A+medium demonstrated that *Z. mobilis* and *S. cerevisiae* were not able to grow on A+medium (data not shown).

Example 2

S. cerevisiae Cultured with Filtered Feedstock Derived from Synechococcus

*Synechococcus* CCMP 2669 ("Syn") was grown on A+medium in flasks as described in Example 1. The culture was harvested and filtered using a 0.2 micron nucleopore filter. Thirty ml of the filtered feedstock was added to flasks. Half of the flasks were purged with nitrogen and inoculated with *S. cerevisiae*.

Figure 2:
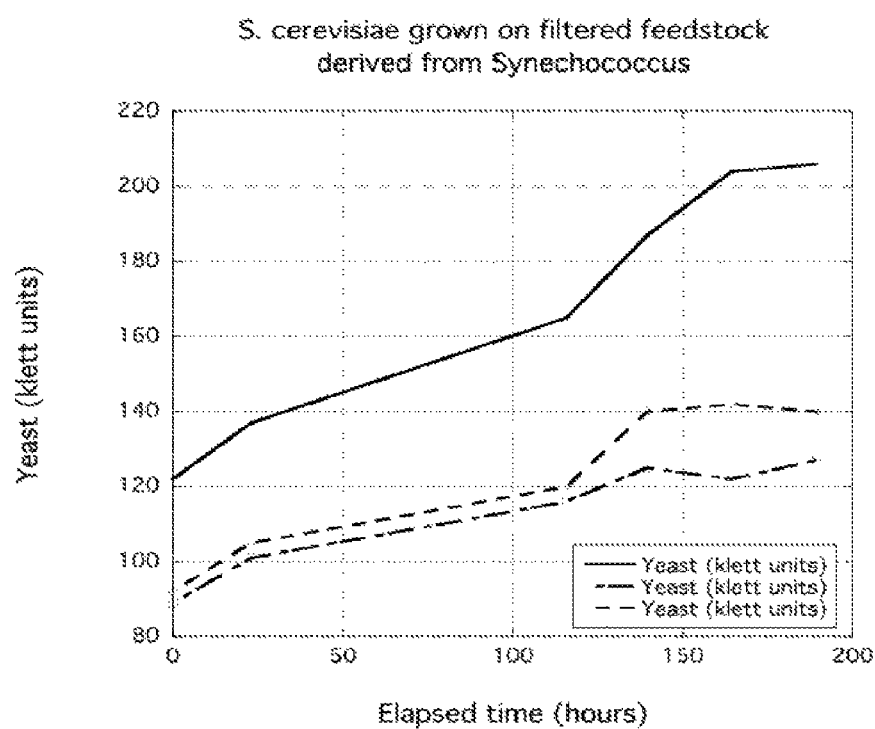
FIG. 2 is a graph that depicts the growth of *S. cerevisiae* on filtered feedstock derived from *Synechococcus*.

Ethanol production by *S. cerevisiae* grown on filtered feedstock inside sealed, nitrogen-purged serum vials was monitored using the enzymatic system described in Example 1, see FIG. 2. *S. cerevisiae* was grown for 4 days on the filtered feedstock. Immediately prior to the assay, 1000 μL of solution containing yeast cells was removed and placed into microfuge tubes. One tube was placed in a centrifuge. Supernatant from that tube was drawn off and placed in a clean microfuge tube as a control to test the effect of yeast cells on the assay. Other controls (0.1% ETOH (v/v)) were set up to test the effect of a 24 hour incubation on ethanol volatilization both in sealed serum vials and microfuge tubes. As shown in FIG. 2, three replicate flasks showed similar growth curves, with one flask having a higher initial cell density.

Ethanol production by *S. cerevisiae* grown on filtered feedstock was close to 0.1% (v/v). The enzymatic assay was affected by the presence of *S. cerevisiae* cells in the assay system, reducing the apparent concentration. Volatilization during incubation and by the type of tube used appeared to have no influence on the assay system.

Additional baseline data was collected on growth rates of the organisms under study using standard media and Klett-Sommerson colorimetry (data not shown). Specifically, Syn was grown on A+medium, *Z. mobilis* was grown on ATCC medium #948 (described in Table 2) and *S. cerevisiae* was grown on YEPD medium (described in Table 3).

Example 3

Co-Culture of Synechococcus CCMP 2669 with Z. mobilis

Figure 3:
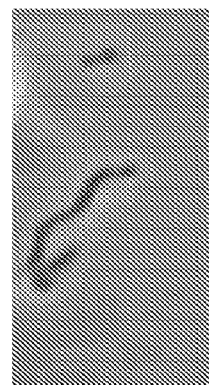
FIG. 3 is a photomicrograph that shows a co-culture of *Synechococcus* CCMP 2669 with *Z. mobilis*. The long chain of cells in the lower section is *Synechococcus*, and the pair of cells at the top is *Z. mobilis*.

Test tubes with *Synechococcus* CCMP 2669 ("Syn"). grown on A+medium were inoculated with 1.0 ml of *Z. mobilis* (in log phase growth) on ATCC #948 medium. Cultures were monitored visually for growth and photomicrographs of growing cultures were taken, see FIG. 3.

*Z. mobilis* was observed to grow in co-culture with Synechococcus in A+media (FIG. 3). *Z. mobilis* could not grow alone on A+media (data not shown).

Example 4

Co-Culture of Synechococcus with S. cerevisiae

Figure 4:
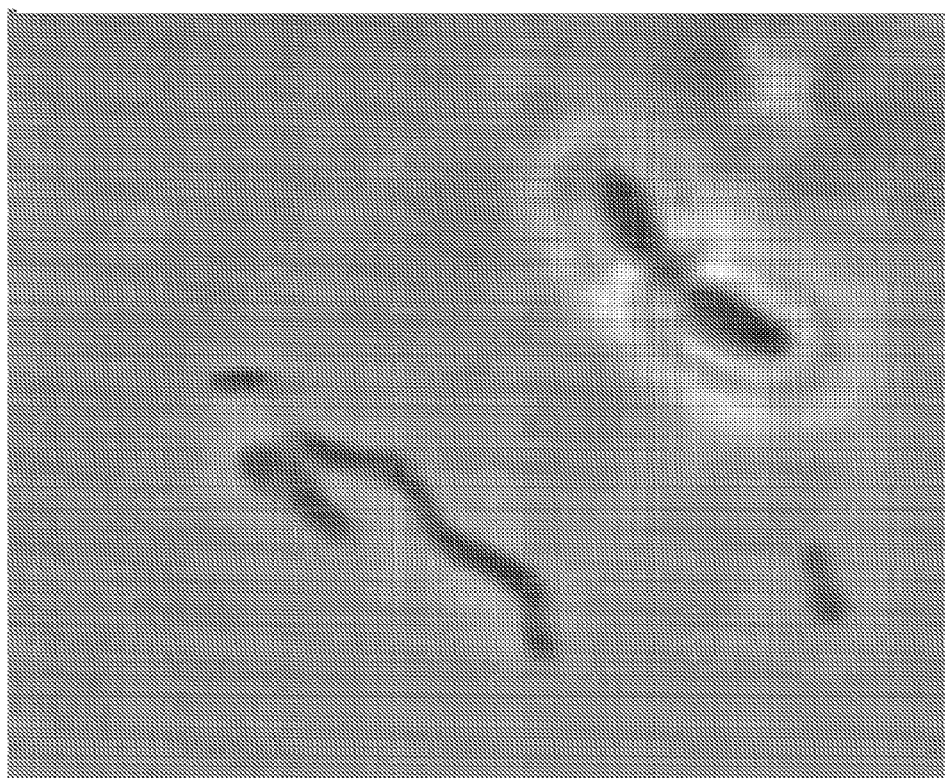
FIG. 4 is a photomicrograph that shows a co-culture of *Synechococcus* (bottom left) with *S. cerevisiae* (top right).

Test tubes with *Synechococcus* CCMP 2669 ("Syn") grown on A+medium were inoculated with 1.0 ml of *S. cerevisiae* (in log phase growth) grown on YEPD medium. Cultures were monitored visually for growth and photomicrographs of growing cultures were taken. See FIG. 4.

*S. cerevisiae* was observed to grow in co-culture with Synechococcus in A+media. (FIG. 4). *S. cerevisiae* was not observed to grow alone on A+media.

Example 5

Co-Culture of Synechococcus with S. cerevisiae Grown on Filtered Seawater

*Synechococcus* CCMP 2669 ("Syn") was grown on filtered seawater in a 5 gallon glass carboy illuminated by a 150 W halogen light on a 10/14 light/dark cycle for 55 days. The culture was photographed at days 0 and 20. Visual inspection showed that Syn grew on filtered seawater. Some evidence of photobleaching was noted and when the cultures were removed from direct light they exhibited a deeper color and improved growth via visual inspections. Microscopy of the culture after 55 days revealed live cells (cyanobacteria), many with filamentous structures.

*Synechococcus* CCMP 2669 ("Syn") was then grown on filtered seawater in aerated (using a small aquarium pump) and non-aerated flasks under natural sunlight filtered through a glass window. Growth was monitored visually for 30 days. Small or no difference between aerated and non-aerated flasks was noted.

Figure 5:
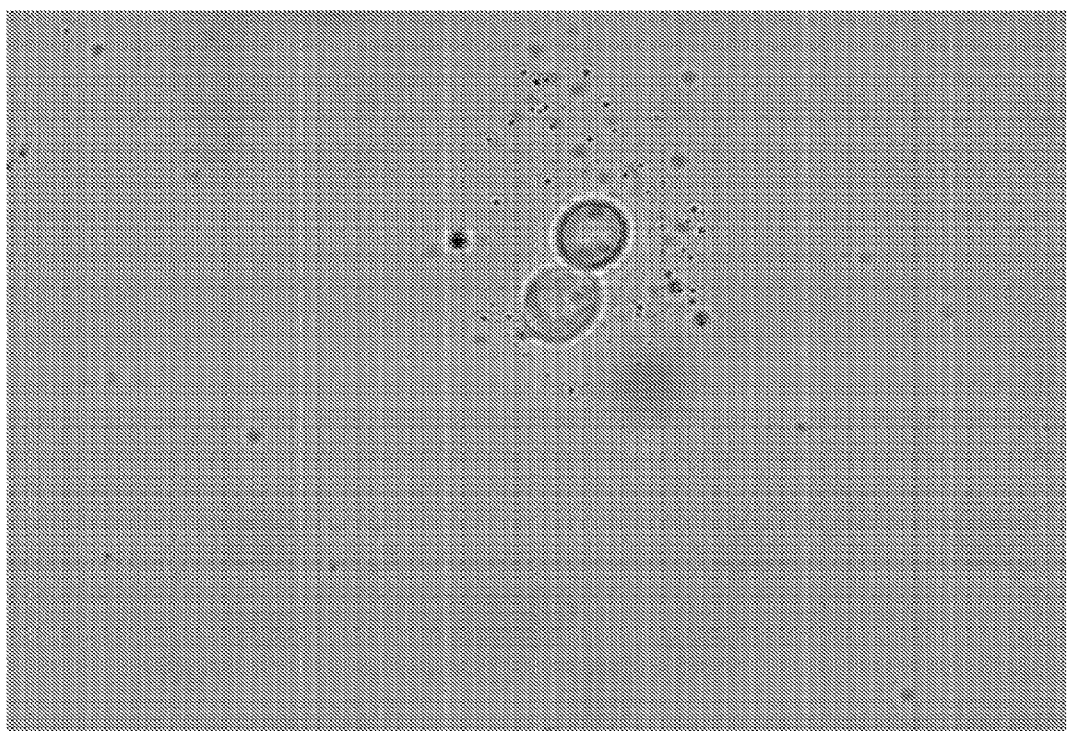
FIG. 5 is a photomicrograph that shows a co-culture of *Synechococcus* with *S. cerevisiae* grown on filtered seawater.

At 30 days, *S. cerevisiae* was added to each of the 4 flasks and growth was monitored visually. About twelve days after the addition, microscopy revealed budding yeast cells and healthy Syn cells (FIG. 5). This data demonstrates that *S. cerevisiae* was able to grow on filtered sea water, and that its growth was fueled by catabolites produced by Syn.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 6

Yeast Subjected to Natural Selection to Enhance Salt Tolerance

Yeast strains or species suitable for subjection to a natural selection protocol to enhance salt tolerance are obtained from a variety of sources. In some cases, a salt-intolerant yeast strain or species is isolated from nature, obtained from a culture collection, or obtained from a commercial source. In other cases, a salt-tolerant yeast strain or species is isolated from nature. In some cases, a yeast species is naturally salt-tolerant and geographically adapted to local seawater composition and environmental conditions (e.g., light, temperature, pH, etc.). Latitudinal gradients may drive light and temperature regimes and species composition and can be used to help identify species with desired characteristics. See Madigan, M. T., Martinko, J. M., Dunlap, P. V. and Clark, D. P. 2009. (Published February, 2008) Brock Biology of Microorganisms, 12th edition, Pearson Benjamin-Cummings, San Francisco. ISBN 0-13-2232460-1.

Any yeast strain or species exhibiting salt tolerance from salt-intolerant to naturally salt-tolerant is subjected to natural selection using a salt tolerance protocol. First, the yeast is cultured in yeast growth media known to the art, which is made with sterile distilled or deionized (DI) water. The yeast is transferred to medium prepared with 80% sterile distilled or DI water and 20% sterile seawater. When the culture grows to near log phase, the yeast is transferred to medium prepared with 60% sterile distilled or DI water and 40% sterile seawater. When the culture grows to near log phase, the yeast is again transferred to medium prepared with 40% sterile distilled, or DI water and 60% sterile seawater. When the culture grows to near log phase, the yeast is again transferred to medium prepared with 20% sterile distilled or DI water and 80% sterile seawater. Finally, when the culture grows to near log phase, the yeast is transferred to medium prepared with 100% sterile seawater. The isolated, natural selected, salt-tolerant yeast strain is maintained in medium/sterile seawater on slants and in liquid culture and stored at 4° C.

In some cases, the resulting (e.g., selected) yeast strain tolerates salt concentrations of 1%, 1.5%, 2%, 2.5%, or 3% (w/v). In some cases, the resulting yeast strain tolerates salt concentrations up to that of typical seawater, e.g., up to approximately 3.5% (w/v). In some cases the resulting yeast strain tolerates salt concentrations above that of typical seawater, for example, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or 15% (w/v).

Example 7

Cyanobacteria Subjected to Directed Evolution to Enhance Specific Traits

Species of cyanobacteria are subjected to directed evolution to enhance specific traits (e.g., sugar production/secretion, salt tolerance, bioproduct formation, etc.) using a protocol as follows. The cyanobacteria are grown to just past mid-log phase in appropriate growth medium known to the art. The organisms are subjected to mutagenesis using, for example, UV radiation (ca. 254 nm) from a germicidal lamp for varying doses using varying times and varying intensities and again grown to mid-log phase. In cases where cyanobacteria are subjected to directed evolution to enhance sugar production, the cultures are examined in near IR light spectral wave length range (700-1100 nm) for sugar spectra. Subcultures exhibiting the highest sugar content in the surrounding medium are selected. Finally, the selected subcultures are grown and tested for stability of growth and sugar production. Multiple rounds of such a directed evolution protocol are used to produce cyanobacteria exhibiting sugar secretion, wherein the rate of sugar secretion increases from 2% (w/v) per 24 hours to 20% (w/v) per 24 hours.

Example 8

Cyanobacteria Subjected to Directed Evolution to Enhance Sugar Production

A trace element solution was prepared by adding the components, as indicated in Table 4, infra, to 950 mL $dH_2O$ and bringing the final volume to 1 liter with $dH_2O$ followed by autoclaving. A f/2 vitamin solution was also prepared by first preparing primary stock solutions as indicated in Table 5, infra. The final vitamin solution was prepared by dissolving the thiamine in 950 mL of $dH_2O$ and adding 1 mL of the primary stocks and bringing the final volume to 1 liter with $dH_2O$ followed by filtering and sterilizing. See Guillard, R. R. L. and Ryther, J. H. 1962. Studies of marine planktonic diatoms. I. *Cyclotella nana* Hustedt and *Detonula confervacea* Cleve. *Can. J. Microbiol.* 8: 229-239; Guillard, R. R. L. 1975. Culture of phytoplankton for feeding marine invertebrates. pp 26-60. In Smith W. L. and Chantey M. H (Eds.) *Culture of Marine Invertebrate Animals*. Plenum Press, New York, USA.

L1 Medium (a general purpose marine medium for growing coastal algae) was prepared as described in Guillard, R. R. L. and Hargraves, P. E. 1993. *Stichochrysis immobilis* is a diatom, not a chrysophyte. *Phycologia* 32: 234-236. The quantity of each component, as indicated in Table 6, infra, was added to 950 mL of filtered natural seawater. The final volume was brought to 1 liter using filtered natural seawater and the medium was autoclaved.

Cultures of CCMP 1333 were grown to mid-log phase and inoculated into each well of a 96 well culture plate containing L1 medium. The inoculum was 10% of the medium volume in each well. The plate was subjected to UV radiation from a germicidal lamp at 254 nm for 3 minutes and then incubated at room temperature under fluorescent lighting for 48 hours. A cell-free subsample was removed and added to a clean culture plate, and examined in near IR light spectral wave length range (700-1100 nm) for sugar spectra using an automated UV spectrophotometer. Standards were run using L1 medium spiked with glucose to derive spectral signatures ranging from 0% glucose to 16% glucose, and a control was run to determine the effect, if any, of UV irradiation on the L1/glucose standards. Some treated wells exhibited an increase from the native approximate 2% (w/v) sugar production per 24 hours to approximately 4-5% (w/v) glucose per 24 hours.

TABLE 4

Trace Element Solution

| Component | Stock Solution | Quantity | Molar Concentration in Final Medium |
|---|---|---|---|
| $Na_2EDTA \cdot 2H_2O$ | — | 4.36 g | $1.17 \times 10^{-5}$ M |
| $FeCl_3 \cdot 6H_2O$ | — | 3.15 g | $1.17 \times 10^{-5}$ M |
| $MnCl_2 \cdot 4H_2O$ | 178.10 g $L^{-1}$ $dH_2O$ | 1 mL | $9.09 \times 10^{-7}$ M |
| $ZnSO_4 \cdot 7H_2O$ | 23.00 g $L^{-1}$ $dH_2O$ | 1 mL | $8.00 \times 10^{-8}$ M |
| $CoCl_2 \cdot 6H_2O$ | 11.90 g $L^{-1}$ $dH_2O$ | 1 mL | $5.00 \times 10^{-8}$ M |
| $CuSO_4 \cdot 5H_2O$ | 2.50 g $L^{-1}$ $dH_2O$ | 1 mL | $1.00 \times 10^{-8}$ M |
| $Na_2MoO_4 \cdot 2H_2O$ | 19.9 g $L^{-1}$ $dH_2O$ | 1 mL | $8.22 \times 10^{-8}$ M |
| $H_2SeO_3$ | 1.29 g $L^{-1}$ $dH_2O$ | 1 mL | $1.00 \times 10^{-8}$ M |
| $NiSO_4 \cdot 6H_2O$ | 2.63 g $L^{-1}$ $dH_2O$ | 1 mL | $1.00 \times 10^{-8}$ M |
| $Na_3VO_4$ | 1.84 g $L^{-1}$ $dH_2O$ | 1 mL | $1.00 \times 10^{-8}$ M |
| $K_2CrO_4$ | 1.94 g $L^{-1}$ $dH_2O$ | 1 mL | $1.00 \times 10^{-8}$ M |

TABLE 5 f/2 Vitamin Solution

| Component | Primary Stock Solution | Quantity | Molar Concentration in Final Medium |
|---|---|---|---|
| thiamine•HCl (vit. B$_1$) | — | 100 mg | $2.96 \times 10^{-7}$ M |
| biotin (vit. H) | 0.05 g L$^{-1}$ dH$_2$O | 10 mL | $2.05 \times 10^{-9}$ M |
| cyanocobalamin (vit. B$_{12}$) | 0.5 g L$^{-1}$ dH$_2$O | 1 mL | $3.69 \times 10^{-10}$ M |

TABLE 6

L1 media

| Component | Stock Solution | Quantity | Molar Concentration in Final Medium |
|---|---|---|---|
| NaNO$_3$ | 75.00 g L$^{-1}$ dH$_2$O | 1 mL | $8.82 \times 10^{-4}$ M |
| NaH$_2$PO$_4$•H$_2$O | 5.00 g L$^{-1}$ dH$_2$O | 1 mL | $3.62 \times 10^{-5}$ M |
| Na$_2$SiO$_3$•9H$_2$O | 30.00 g L$^{-1}$ dH$_2$O | 1 mL | $1.06 \times 10^{-4}$ M |
| trace element solution | (see Table 4, supra) | 1 mL | — |
| vitamin solution | (see Table 5, supra) | 1 mL | — |

What is claimed is:

1. A method comprising:
   a. culturing a consortium of cyanobacteria comprising *Synechococcus* CCMP 1333, *Synechococcus* PCC 7002, and *Cyanothece* in a culture medium that comprises a salt concentration greater than or equal to 0.08% (w/v) to produce sugars and polysaccharides; and
   b. removing cyanobacteria from the culture in order to obtain a feedstock medium containing sugars and polysaccharides that is substantially free of cyanobacteria.

2. The method of claim 1, wherein said cyanobacteria are previously cultured in a medium comprising sea water or processed sea water.

3. The method of claim 1, wherein said cyanobacteria are removed from said culture by centrifugation, filtration, separation, decanting, or combinations thereof.

4. The method of claim 1, wherein said culturing comprises culturing in a medium comprising sea water or processed sea water.

5. The method of claim 1, further comprising the step of processing the feedstock medium to obtain a solution substantially free of cyanobacteria.

6. The method of claim 1, further comprising processing the feedstock medium in order to produce substantially-pure sugars and polysaccharides.

7. The method of claim 1, wherein sugars, or polysaccharides in the feedstock medium are substantially derived from said cyanobacteria.

8. The method of claim 1, wherein the cyanobacteria consortium consists essentially of *Cyanothece* sp. Miami BG043511, *Synechococcus* CCMP 1333, and *Synechococcus* PCC 7002.

* * * * *